(12) United States Patent
Fevola et al.

(10) Patent No.: US 8,986,665 B2
(45) Date of Patent: Mar. 24, 2015

(54) CATIONIC POLYGLYCERYL COMPOSITIONS AND COMPOUNDS

(75) Inventors: Michael J. Fevola, Belle Mead, NJ (US); Frank C. Sun, Branchburg, NJ (US); Stacey E. York, Princeton, NJ (US)

(73) Assignee: Johnson & Johnson Consumer Companies, Inc., Skillman, NJ (US)

( * ) Notice: Subject to any disclaimer, the term of this patent is extended or adjusted under 35 U.S.C. 154(b) by 0 days.

(21) Appl. No.: 13/331,157

(22) Filed: Dec. 20, 2011

(65) Prior Publication Data
US 2012/0087882 A1 Apr. 12, 2012

(51) Int. Cl.
| | | |
|---|---|---|
| *A61K 8/92* | (2006.01) | |
| *A61K 8/86* | (2006.01) | |
| *A61Q 5/12* | (2006.01) | |
| *A61Q 19/00* | (2006.01) | |
| *A61Q 19/10* | (2006.01) | |
| *C07D 319/12* | (2006.01) | |
| *C07C 217/40* | (2006.01) | |
| *A61Q 5/02* | (2006.01) | |
| *A61K 8/04* | (2006.01) | |
| *A61K 8/39* | (2006.01) | |
| *A61K 8/45* | (2006.01) | |

(52) U.S. Cl.
CPC . *A61Q 5/02* (2013.01); *A61K 8/042* (2013.01); *A61K 8/39* (2013.01); *A61K 8/45* (2013.01); *A61Q 5/12* (2013.01); *A61Q 19/00* (2013.01); *A61Q 19/10* (2013.01)
USPC ........ 424/70.11; 514/452; 514/549; 549/378; 554/223

(58) Field of Classification Search
None
See application file for complete search history.

(56) References Cited

U.S. PATENT DOCUMENTS

| | | | |
|---|---|---|---|
| 3,654,261 A | 4/1972 | Johnson | |
| 3,931,148 A | 1/1976 | Langdon | |
| 4,205,063 A | 5/1980 | Khalil et al. | |
| 4,292,212 A | 9/1981 | Melby | |
| 4,512,856 A * | 4/1985 | Paneccasio | 205/314 |
| 4,676,978 A | 6/1987 | Cseh | |
| 4,689,217 A | 8/1987 | Restaino et al. | |
| 4,803,071 A | 2/1989 | Iovine et al. | |
| 4,987,526 A | 1/1991 | Slocum et al. | |
| 5,138,043 A | 8/1992 | Polovsky et al. | |
| 5,215,976 A | 6/1993 | Fost et al. | |
| 5,286,719 A | 2/1994 | Fost et al. | |
| 5,288,484 A | 2/1994 | Tashjian | |
| 5,384,334 A | 1/1995 | Polovsky et al. | |
| 5,482,704 A | 1/1996 | Sweger et al. | |
| 5,648,348 A | 7/1997 | Fost et al. | |
| 5,650,402 A | 7/1997 | Fost et al. | |
| 6,365,140 B1 | 4/2002 | Melby et al. | |
| 6,440,907 B1 | 8/2002 | Santora et al. | |
| 7,087,560 B2 | 8/2006 | Mc Manus et al. | |
| 7,282,471 B2 | 10/2007 | Harichian et al. | |
| 7,335,627 B1 | 2/2008 | O'Lenick et al. | |
| 7,375,064 B1 | 5/2008 | O'Lenick | |
| 7,507,399 B1 | 3/2009 | O'Lenick | |
| 7,659,234 B2 | 2/2010 | Harichian et al. | |
| 2007/0009464 A1 | 1/2007 | Laine et al. | |
| 2008/0119414 A1 | 5/2008 | Behler et al. | |
| 2009/0270606 A1 | 10/2009 | Laine et al. | |
| 2010/0284955 A1 | 11/2010 | Lepilleur et al. | |

FOREIGN PATENT DOCUMENTS

| | | |
|---|---|---|
| EP | 308189 A | 3/1989 |
| EP | 486074 A | 5/1992 |
| EP | 758641 A | 2/1997 |
| JP | 2005-256152 A | 9/2005 |
| WO | WO 95/18157 A | 7/1995 |
| WO | WO 2007/094603 A | 8/2007 |
| WO | WO 2007/101527 A | 9/2007 |

OTHER PUBLICATIONS

Pastorfide et al, "Zinc Chloride Spray—Magnesium Hydroxide Ointment Dual Topical Regimen in the Treatment of Obstetric and Gynecologic Incisional Wounds", Clin. Ther. (Mar.-Apr. 1989) vol. 11, Issue 2, pp. 258-263.

Rokicki et al., "Hyperbranched aliphatic polyethers obtained from invironmentally benign monomer: glycerol carbonate", The Royal Society of Chemistry 2005, *Green Chemistry* 2005 7:529-539.

Xu et al., "Study on the Synthesis and Surface Active Properties of a Novel Surfactant with Triple Quaternary Ammonium Groups and Triple Dodecyl Chains Derived from Glycerin", *J. Surfact Deterg*(2011) 14:167-172.

Crowther et al, "Electrospray Mass Spectrometry for Characterizing Polyglycerols and the Effects of Adduct Ion and Cone voltage", JAOCS, vol. 75, No. 12 (1998), pp. 1867-1876.

\* cited by examiner

*Primary Examiner* — Patricia A Duffy
*Assistant Examiner* — Garen Gotfredson

(57) ABSTRACT

Provided are polyglyceryl compositions comprising one or more polyglyceryl compounds having: (a) a node structure comprising at least three contiguous glyceryl remnant units; (b) one or more cationic groups each linked to the node structure by an independently selected linking group; and (c) one or more hydrophobic moieties each independently (i) linked to the node structure by a linking group, or (ii) constituting a portion of one of the one or more cationic groups, wherein the composition has an average degree of polymerization determined by hydroxyl value testing ($DP_{OH}$) of from about 3 to about 20. Also provided are polyglyceryl compounds which may compose such compositions, and uses of the polyglyceryl compositions and compounds.

11 Claims, 4 Drawing Sheets

US 8,986,665 B2

CATIONIC POLYGLYCERYL COMPOSITIONS AND COMPOUNDS

FIELD OF INVENTION

The present invention relates to cationic polyglyceryl compositions and compounds that are useful in a variety of applications including moisturizing or conditioning the skin or hair.

DESCRIPTION OF THE RELATED ART

Personal care compositions, e.g., lotions, conditioners, cleansers and the like, typically include numerous ingredients. These ingredients may be used to stabilize the product, provide improved aesthetics, as well as moisturize, condition, cleanse or otherwise treat the body. For example, so-called "humectants" are a class of ingredients which generally serve to attract moisture and retard evaporation of water from the body surface. Common commercial humectants include glycerin, propylene glycol, sorbitols, and polyethylene glycols.

The inventors have recognized that in order to increase the options available to designers of personal care products, it would be desirable to have a humectant material that has additional functionality, such as one or more of improved substantivity, moisture retention, foaming, viscosity building, and mildness. Furthermore, the inventors have additionally recognized that it would be desirable to be able to tune these various properties by adjusting the proportions and chemistry of the reactants used to make the humectant material. Additionally, the inventors have recognized that it would beneficial for the process of making such a material not to require an ethoxylation process, due to the potential health and safety risks of working with ethylene oxide starting material.

Accordingly, the invention described herein addresses one or more of the above-mentioned drawbacks.

SUMMARY OF THE INVENTION

The present invention provides cationic polyglyceryl compounds that overcome the disadvantages of the prior art and tend to exhibit beneficial unexpected properties. In particular, applicants have discovered that the compositions and compounds of the present invention tend to exhibit improved substantivity, moisture retention, foaming, viscosity building, mildness, and/or combinations thereof, as compared to other comparable (polyglyceryl or otherwise) humectant compounds.

According to one aspect, the present invention provides polyglyceryl compositions comprising one or more polyglyceryl compounds having: (a) a node structure comprising at least three contiguous glyceryl remnant units; (b) one or more cationic groups each linked to the node structure by an independently selected linking group; and (c) one or more hydrophobic moieties each independently (i) linked to the node structure by a linking group, or (ii) constituting a portion of one of the one or more cationic groups.

According to another aspect, the present invention provides polyglyceryl compounds comprising one or more compounds, of the Formula I:

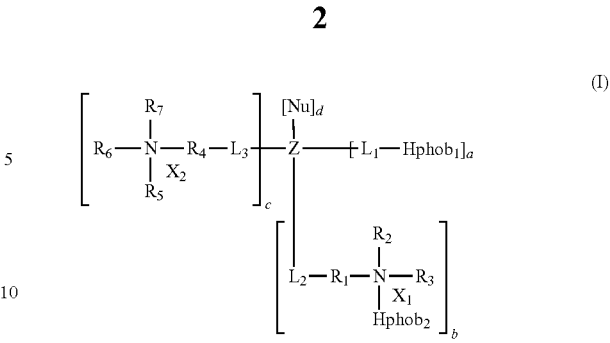

wherein, according to this embodiment:

Z is a polyglyceryl node structure that comprises at least 3 contiguous glyceryl remnant units;

Nu are independently selected nucleophilic groups which are directly linked to Z;

d is the number of nucleophilic groups directly bonded to Z, and is from 2 to 21;

$L_1$ is an independently selected linking group which links Z to $Hphob_1$;

$Hphob_1$ is an independently selected hydrophobic moiety comprising 6 to 30 carbons;

a is the number of $Hphob_1$ linked to the node structure Z, each via an $L_1$, and is from zero to 10;

$L_2$ is an independently selected linking group which links Z to a cationic group —$R_1$—N—[$(R_2)(R_3)(Hphob_2)$];

$R_1$ is an independently selected linear or branched alkylene (—CH— to —$C_6H_{12}$—) or monohydroxyalkylene (—CH(OH)— to —$C_6H_{11}$(OH)—);

N is a nitrogen atom;

$R_2$ is an independently selected alkyl group containing 1 to 4 carbons ($CH_3$ to $C_4H_9$) or a hydrogen atom;

$R_3$ is an independently selected alkyl group containing 1 to 4 carbons ($CH_3$ to $C_4H_9$) or a hydrogen atom, or an independently selected hydrophobic moiety;

$Hphob_2$ is an independently selected hydrophobic moiety comprising 6 to 30 carbons;

$X_1$ is an anionic counterion or absent;

b is the number of ($R_1$—N—[$(R_2)(R_3)(Hphob_2)$]) linked to the node structure, Z, each via an $L_2$, and is from zero to 10;

$L_3$ is an independently selected linking group which links Z to cationic group —$R_4$—N—[$(R_5)(R_6)(R_7)$];

$R_4$ is an independently selected linear or branched alkylene (—CH— to —$C_6H_{12}$—) or monohydroxylalkylene (—CH(OH)— to —$C_6(OH)H_{11}$(OH)—);

$R_5$, $R_6$, $R_7$ are each an independently selected alkyl group containing 1 to 4 carbons ($CH_3$ to $C_4H_9$);

$X_2$ is a anionic counterion or absent;

c is the number of ($R_4$—N—[$(R_5)(R_6)(R_7)$]) linked to the node structure, Z, each via an $L_3$, and is from zero to 10;

wherein the sum of a and b is from 1 to 10 inclusive;
the sum of b and c is from 1 to 10 inclusive;
the sum of a, b, and c is from 1 to 10 inclusive;
and the sum of a, b, c and d is from 3 to 22 inclusive.

DESCRIPTION OF PREFERRED EMBODIMENTS

Figure 1:
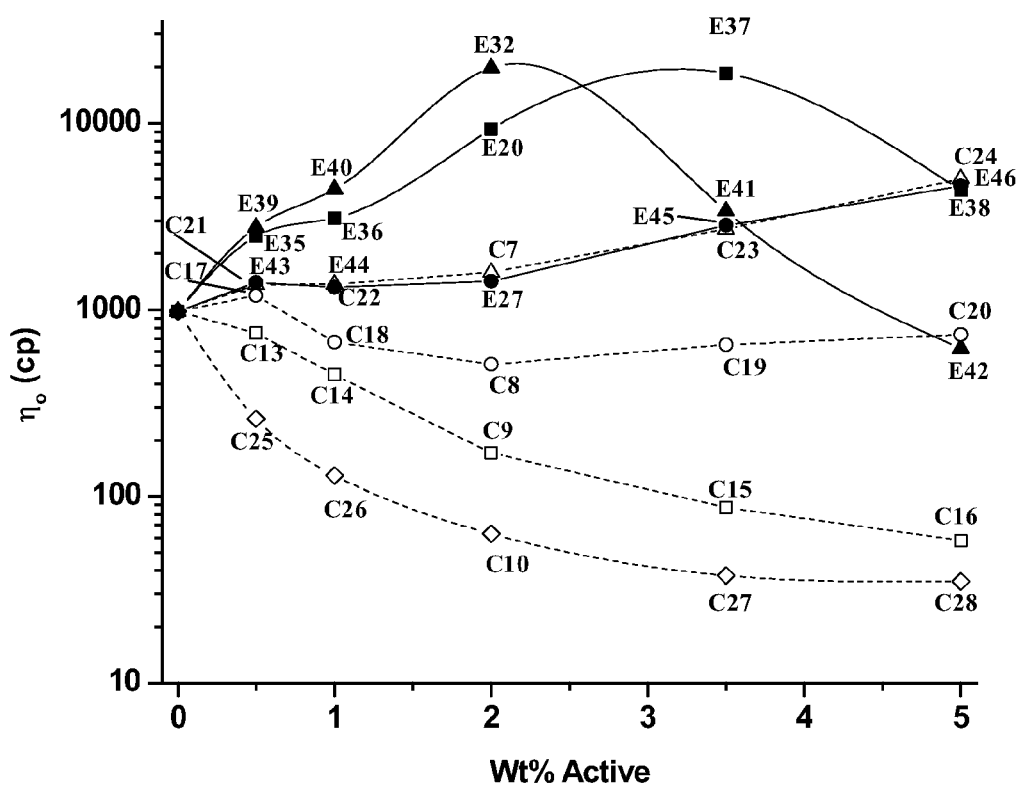
FIG. 1 is a graphical depiction of zero shear viscosities of certain compositions of the present invention and comparable compositions.

All percentages listed in this specification are percentages of solids/active amounts by weight, unless otherwise specifically mentioned.

As used herein, the term "healthcare" refers to the fields of personal care and medical care including, but not limited to, infant care, oral care, sanitary protection, skin care, including the topical treatment of adult or infant skin to maintain the health of the skin, improve the health of the skin, and/or improve the appearance of the skin, wound care, including the treatment of a wound to assist in the closure or healing of a wound, and/or to reduce the pain or scarring associated with the wound, women's health, including the treatment of tissue in the internal or external vaginal area and/or breast, maintaining or improving the health of such tissue or skin, repairing such tissue or skin, reducing irritation of such tissue or skin, maintaining or improving the appearance of such tissue or skin, and improving or enhancing sexual function associated with such tissue or skin, and the like.

As noted above, applicants have discovered that certain cationic polyglyceryl compositions can be used as nonethoxylated, substantive humectants in various compositions, including cosmetic and personal care compositions. The resulting compositions may be suitable for use as cleansing, rinse-off, or leave-on compositions. In particular, applicants have recognized significant unexpected benefits associated with compositions comprising one or more polyglyceryl compounds having: (a) a node structure comprising at least three contiguous glyceryl remnant units; (b) one or more cationic groups each linked to the node structure by an independently selected linking group; and (c) one or more hydrophobic moieties each independently (i) linked to the node structure by a linking group, or (ii) constituting a portion of one of the one or more cationic groups.

In certain embodiments of the instant invention, the cationic polyglyceryl compositions comprise at least one polyglyceryl compound as described herein, preferably two or more. In certain embodiments, the polyglyceryl compositions of the present invention comprise at least three, preferably at least four, and in certain preferred embodiments, at least five polyglyceryl compounds as described herein. In such embodiments, the polyglyceryl composition preferably has an average degree of polymerization determined by hydroxyl value testing ($DP_{OH}$) of from about 3 to about 20, for example, from about 3 to about 18, or from about 3 to about 15. In certain preferred embodiments, the polyglyceryl compositions of the present invention have a $DP_{OH}$ of from about 3 to about 12, and even more preferably from about 3 to about 10, more preferably about 5 to about 10, more preferably about 7 to about 10, and more preferably about 10.

As described herein, the hydroxyl value (OH#) associated with a polyglyceryl material, defined as the number of milligrams of potassium hydroxide equivalent to the hydroxyl content of one gram of sample, is measured in accord with the standard American Oil Chemists' Society (AOCS) Official Method Cd 13-60 Hydroxyl Value. $DP_{OH}$ of the polyglyceryl material is then calculated, using the hydroxyl value (OH#) of the material, in accord with the following equation:

$$DP_{OH} = \frac{112,200 - (18 \times OH\#)}{(74.05 \times OH\#) - 56,100}$$

For the purposes of clarity only, the following general description of hydroxyl value and $DP_{OH}$ for a polyglyceryl material are provided. For hydroxyl value, in accord with the AOCS method above, a known mass of the material to be tested (e.g. a polyglyceryl material) is reacted with acetic anhydride in the presence of pyridine. The acetylated polyol is then hydrolyzed to the resulting polyol and acetic acid. The amount of acetic acid released during the hydrolysis reaction is determined by titrating KOH in the presence of a phenothalein indicator. The hydroxyl value is then determined by calculating the mg of KOH required to neutralize the solution containing one gram of polyol. The $DP_{OH}$ is then calculated using the hydroxyl number via the calculation above.

Figure 2:
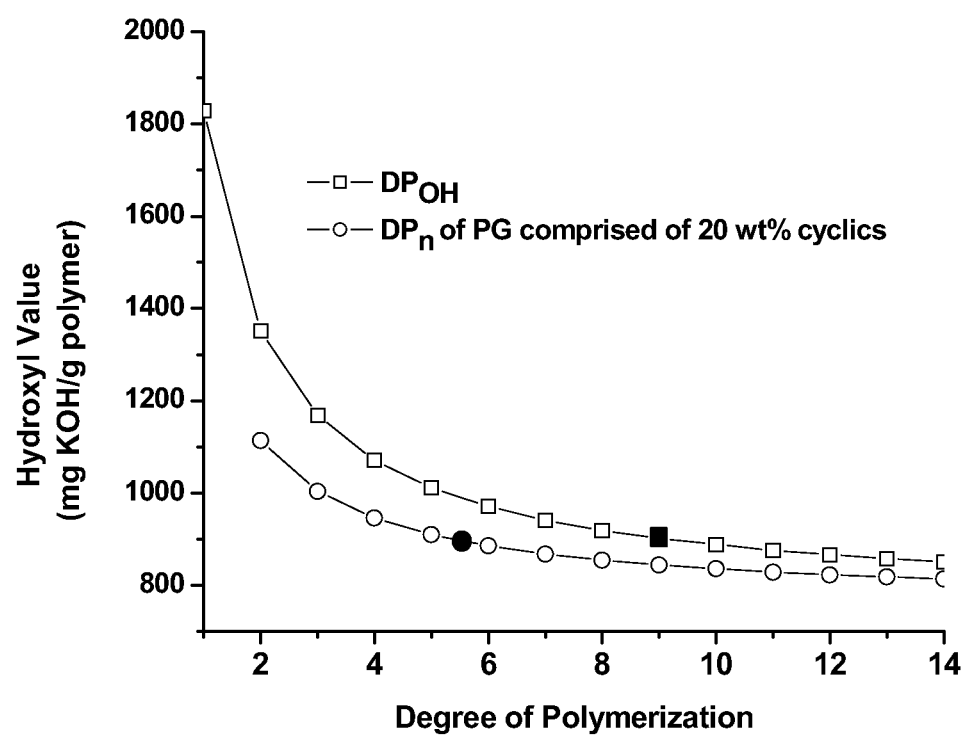
FIG. 2 is a graphical depiction of hydroxyl value verses the degree of polymerization for a linear polyglycerol.

Those of skill in the art will recognize that $DP_{OH}$ is determined by a technique which does not distinguish between linear and dendritic (branched or cyclic) repeat units, but rather provides information regarding the number of hydroxyl groups per gram of polymer. Those skilled in the art will recognize that the number average DP ($DP_n$), which is based on the average number of repeating units per polymer, may deviate significantly from the $DP_{OH}$ if certain isomers, such as cyclic repeat units, are present (Crowther, M. W. et al., JAOCS, 75, 1867, 1998). This is depicted, for example, in FIG. 2, which shows a theoretical curve of hydroxyl value vs $DP_n$ for the case of pure linear polyglycerol (open squares) and a polyglycerol sample containing 20 wt % cyclic repeat units. The closed symbol on each line approximates a hydroxyl value of 900. As seen in FIG. 2, a 20/80 wt % cyclic/linear mixture which yields a hydroxyl value of 900 has a $DP_n$ of approximately 5.5 (closed circle), as compared to a $DP_{OH}$ of 9 (closed square).

According to preferred embodiments of the present invention, the compositions of the present invention have an average degree of substitution of hydrophobic moieties per node structure (e.g., "a"+"b") that is greater than zero but less than ten, more preferably greater than zero but less than five, and even more preferably greater than zero but less than or equal to three. Those skilled in the art will recognize that substitution of a node structure with hydrophobic moieties to form compounds/compositions of the present invention is likely a heterogeneous process which results in two or more differently substituted cationic polyglyceryl compounds, and thus the average number of hydrophobic moieties per node for a composition, may be represented by a non-integer average value. An example calculation is provided: for a composition comprising polyglyceryl homopolymer compounds of Formula I ($DP_{OH}$=10, i.e., having 10 glyceryl remnant units), with each polymer comprised of an independent composition of $Hphob_1$ and $Hphob_2$ moieties. If 50 mol % of the node structures, Z have 2 mol of $L_1$-$Hphob_1$, 40 mol % of the polyglyceryl remnants Z have 1 mol of $L_1$-$Hphob_1$, and 10 mol % of the polyglyceryl remnants Z have 0 mol of $L_1$-$Hphob_1$, then there are 1.4 {2(0.5)+1(0.4)+0(0.1)=1.4} $L_1$-$R_1$-$Hphob_1$ per mol of Z.

According to preferred embodiments of the present invention, the compositions of the present invention have an average degree of substitution of cationic moieties per node (e.g., "b"+"c") that is greater than zero but less than 10, more preferably greater than zero but less than 5, and even more preferably greater than zero but less than 3. An example calculation is provided: for a composition comprising polyglyceryl homopolymer compounds of Formula I (DP=10, i.e., having 10 glyceryl remnant units), with each polymer comprised of an independent composition of cationic hydrophobic ($-R_1-N-[(R_2)(R_3)(Hphob_2)]$) and cationic ($-R_4-N-[(R_5)(R_6)(R_7)]$) groups. If 60 mol % of the node structures, Z have 2 mol of ($-R_1-N-[(R_2)(R_3)(Hphob_2)]$), 30 mol % of the polyglyceryl remnants Z have 1 mol of ($-R_1-N-[(R_2)(R_3)(Hphob_2)]$),10 mol % of the polyglyceryl remnants Z have 0 mol of ($-R_1-N-[(R_2)(R_3)(Hphob_2)]$) then there are 1.5 {2(0.6)+1(0.3)+0(0.1)=1.5} ($-R_1-N-[(R_2)(R_3)(Hphob_2)]$) per mol of Z. Similarly, If 20 mol % of the node structures, Z have 2 mol of ($-R_4-N-[(R_5)(R_6)(R_7)]$), 50 mol % of the polyglyceryl remnants Z have 1 mol of ($-R_4-N-[(R_5)(R_6)(R_7)]$), 30 mol % of the polyglyceryl remnants Z have 0 mol of ($-R_4-N-[(R_5)(R_6)(R_7)]$) then there are 0.9 {2(0.2)+1(0.5)+0(0.3)=0.9} ($-R_4-N-[(R_5)(R_6)(R_7)]$) per mol of Z. Thus, the average degree of cationic substitution per mol of Z is 2.4 {1.5+0.9=2.4}

According to preferred embodiments of the present invention, the compositions of the present invention have an average degree of substitution of cationic hydrophobic moieties per node (e.g., "b") that is greater than zero but less than 10, more preferably greater than zero but less than 5, and even more preferably greater than about 0.5 but less than 3. An example calculation is provided: for a composition comprising polyglyceryl homopolymer compounds of Formula I (DP=10, i.e., having 10 glyceryl remnant units), with each polymer comprised of an independent composition of cationic hydrophobic groups ($-R_1-N-[(R_2)(R_3)(Hphob_2)]$). If 10 mol % of the node structures, Z have 3 mol of ($-R_1-N-[(R_2)(R_3)(Hphob_2)]$), 30 mol % of the polyglyceryl remnants Z have 2 mol of ($-R_1-N-[(R_2)(R_3)(Hphob_2)]$), 40 mol % of the polyglyceryl remnants Z have 1 mol of ($-R_1-N-[(R_2)(R_3)(Hphob_2)]$), 20 mol % of the polyglyceryl remnants Z have 0 mol of ($-R_1-N-[(R_2)(R_3)(Hphob_2)]$) then there are 1.3 {3(0.1)+2(0.3)+1(0.4)+0(0.2)=1.3} ($-R_1-N-[(R_2)(R_3)(Hphob_2)]$) per mol of Z.

According to certain embodiments, the compounds of the present invention, and the compositions that are made up of such compounds, may be further illustrated with reference to Formula I:

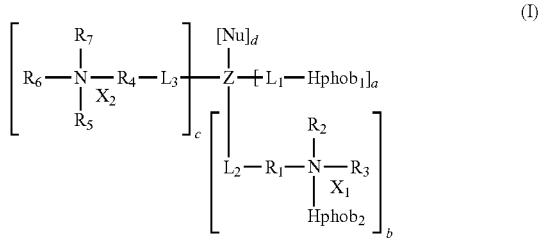

(I)

wherein, according to this embodiment:
Z is a polyglyceryl node structure that comprises at least 3 contiguous glyceryl remnant units;
Nu are independently selected nucleophilic groups which are directly linked to Z;
d is the number of nucleophilic groups bonded to Z, and is from 2 to 21;
$L_1$ is an independently selected linking group which links Z to $Hphob_1$;
$Hphob_1$ is an independently selected hydrophobic moiety comprising 6 to 30 carbons;
a is the number of $Hphob_1$ linked to the node structure Z, each via an $L_1$, and is from zero to 10;

$L_2$ is an independently selected linking group which links Z to a cationic group $-R_1-N-[(R_2)(R_3)(Hphob_2)]$;
$R_1$ is an independently selected linear or branched alkylene ($-CH-$ to $-C_6H_{12}-$) or monohydroxyalkylene ($-CH(OH)-$ to $-C_6H_{11}(OH)-$);
N is a nitrogen atom;
$R_2$ is an independently selected alkyl group containing 1 to 4 carbons ($CH_3$ to $C_4H_9$) or a hydrogen atom;
$R_3$ is an independently selected alkyl group containing 1 to 4 carbons ($CH_3$ to $C_4H_9$) or a hydrogen atom, or an independently selected hydrophobic moiety;
$Hphob_2$ is an independently selected hydrophobic moiety comprising 6 to 30 carbons;
$X_1$ is an anionic counterion or absent;
b is the number of ($-R_1-N-[(R_2)(R_3)(Hphob_2)]$) linked to the node structure, Z, each via an $L_2$, and is from zero to 10;
$L_3$ is an independently selected linking group which links Z to cationic group $-R_4-N-[(R_5)(R_6)(R_7)]$;
$R_4$ is an independently selected linear or branched alkylene ($-CH-$ to $-C_6H_{12}-$) or monohydroxylalkylene ($-CH(OH)-$ to $-C_6(OH)H_{11}(OH)-$);
$R_5$, $R_6$, $R_7$ are each an independently selected alkyl or alkenyl group containing 1 to 4 carbons ($CH_3$ to $C_4H_9$);
$X_2$ is an anionic counterion or absent;
c is the number of ($-R_4-N-[(R_5)(R_6)(R_7)]$) linked to the node structure, Z, each via an $L_3$, and is from zero to 10;
wherein the sum of a and b is from 1 to 10 inclusive;
the sum of b and c is from 1 to 10 inclusive; and
the sum of a, b, and c is from 1 to 10 inclusive.

The compositions of the present invention comprise compounds having a node structure comprising at least three contiguous glyceryl remnant units. By "glyceryl remnant unit," it is meant glycerol units excluding nucleophilic groups such as hydroxyl groups. Glyceryl remnant units generally may be represented as $C_3H_5O$ for linear and dendritic remnants (Rokicki et al. *Green Chemistry.*, 2005, 7, 52). Suitable glyceryl remnant units are dehydrated forms (i.e. one mole of water removed) of the following glyceryl units: linear-1,4 ($L_{1,4}$) glyceryl units; linear-1,3 ($L_{1,3}$) glyceryl repeat units; dendritic (D) glyceryl units; terminal-1,2 ($T_{1,2}$) units; and terminal-1,3 ($T_{1,3}$) units. Examples of such glyceryl remnant repeat and terminal units are shown below (to the right side of the arrows). The corresponding glyceryl unit (shown to the left side of arrows; includes hydroxyls) are shown as well:

linear-1,4 ($L_{1,4}$) glyceryl repeat units

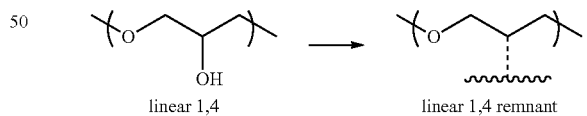

linear 1,4     linear 1,4 remnant linear-1,3 ($L_{1,3}$) glyceryl repeat units

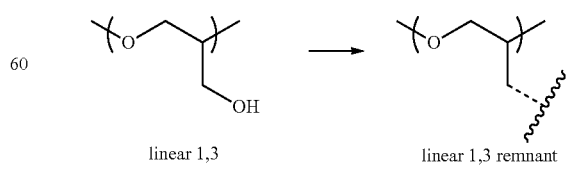

linear 1,3     linear 1,3 remnant dendritic (D) glyceryl repeat units, which lead to branched or cyclic compounds

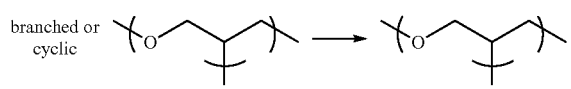

branched or cyclic

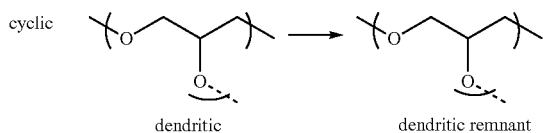

cyclic dendritic → dendritic remnant terminal-1,2 ($T_{1,2}$) units

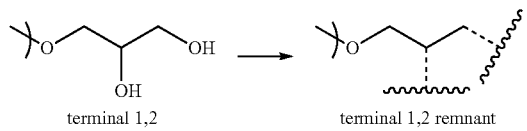

terminal 1,2 → terminal 1,2 remnant and terminal-1,3 ($T_{1,3}$) units

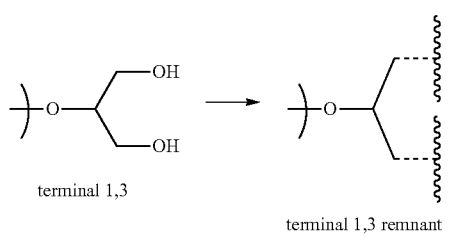

terminal 1,3 → terminal 1,3 remnant

In certain embodiments, in addition to glyceryl remnant units, a node structure may comprise one or more additional oxyalkyl units. The oxyalkyl units may be generically described as —(O—R)— where R=$C_1$-$C_4$ linear or branched alkyl, such as —$CH_2CH_2$—, —$CH(CH_3)CH_2$—, and —$CH_2CH_2CH_2$—, that originate from reacting optional co-monomers such as as 1,2-ethanediol, 1,2-propanediol, 1,3-propanediol, ethylene carbonate, 1,2 propylene carbonate, and 1,3 propylene carbonate. For example, a general formula of glyceryl remnant unit and adjacent oxyalkyl unit may be illustrated as:

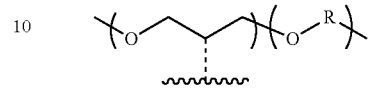

and, as further example, a polyglyceryl-co-1,3-propanediol and accordingly have the node structure:

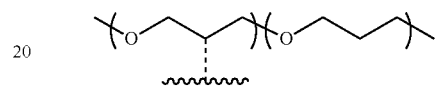

As will be recognized by those of skill in the art, due to the nature of the polymerization of the compounds of the present invention and the nomenclature adopted herein, in certain embodiments, a node of the present invention may further include a terminal (with respect to the node itself) three carbon alkyl group. For example, shown below is an example node of the present invention derived from glycerol wherein upon polymerization the node structure forms seven glyceryl remnant units with one terminal three carbon alkyl group labeled as $C_3H_5$ remnant below:

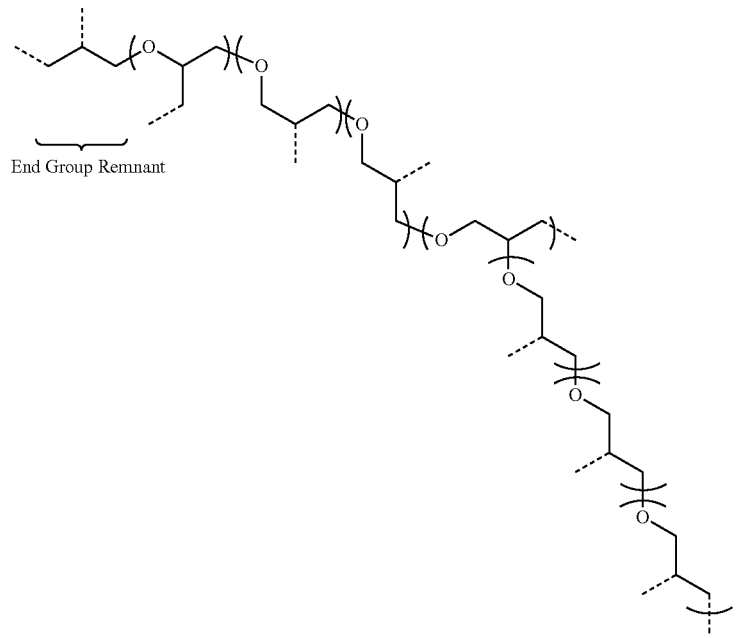

End Group Remnant

Those skilled in the art of polymer chemistry will recognize that a polyglycerol, like any typical polymer, is comprised of repeating units and end groups. In the simple case of a polymer formed by condensation of monomer units (elimination of water during polymerization), the end groups are comprised of the parent molecule while the repeating unit is derived from the parent monomer minus a water molecule. Such is the case for linear polyglycerols, which can be synthesized by using the monomer glycerol.

The polymerization of glycerol is illustrated in the figure below, where w moles of glycerol are polymerized to form a linear polyglycerol with (1-w) repeating units and 1 end group. For clarification, the end group is demarcated by hashed lines. Note that the repeating unit formula $(C_3H_6O_2)$ is equal to the glycerol unit formula $(C_3H_8O_3)$ minus water $(H_2O)$. Also note that the sum of the end group units $[(C_3H_7O_2)$ plus $(OH)]$ equals the formula of glycerol $(C_3H_8O_3)$ and that (1-w) moles of water are formed as a by-product of polymerization.

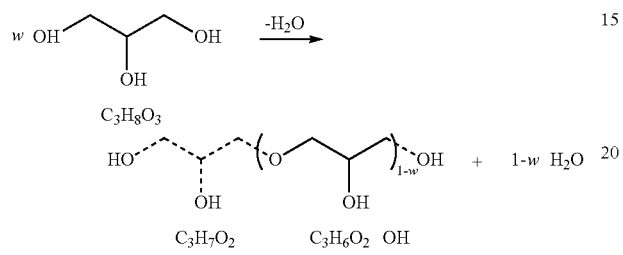

Furthermore, if this principle is carried onto the description of the dehydrated polyether (glyceryl remnant), one would find that the glyceryl repeating unit remnant would have the formula $(C_3H_5O)$. Notably, the terminal remnant would have the formula $(C_3H_5)$

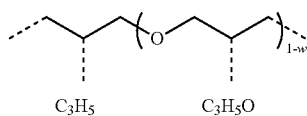

This is further illustrated in the structure below, where repeating unit isomers have been demarcated by parentheses (7 total repeat units) and the terminal glyceryl remnant demarcated by brackets (1 terminal glyceryl remnant), yielding a total DP of 8.

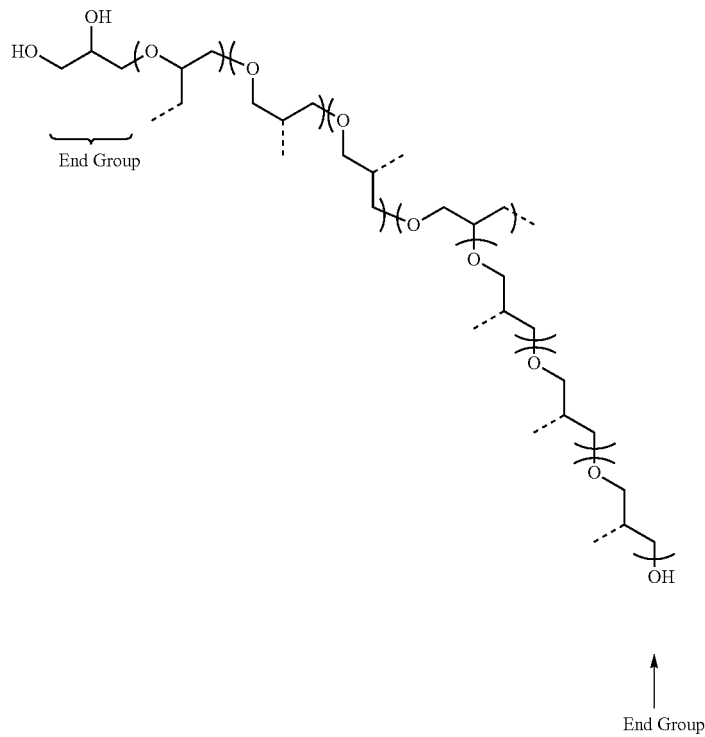

In addition to $C_3H_5$ terminal remnant units and $C_3H_5O$ remnant repeat units, there may also be $C_3H_5O_2$ remnant units and $C_3H_5O$ terminal remnant units present when the molecule is contains certain isomers containing dendritic-based cyclic units. This is illustrated below, where repeat and terminal units are demarcated by parentheses for a pentaglycerol which contains two dendritic-based cyclic units. Unless otherwise specified, the repeat and terminal remnant units are of the formula $C_3H_5O$.

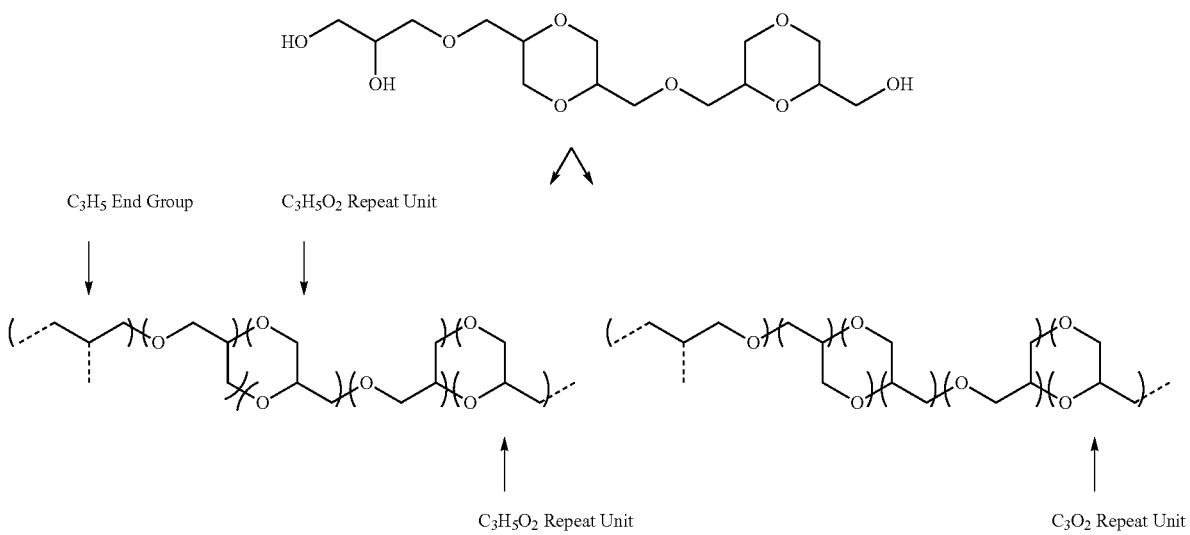

According to certain preferred embodiments, each node structure of the present invention includes from three to about 20 glyceryl remnant units (and optionally one or more oxyalkyl units) and is capable of having from 3 to about 21 total combined groups, selected from nucleophilic groups, hydrophobic groups (Hphob$_1$), cationic groups (—R$_4$—N—[(R$_5$)(R$_6$)(R$_7$)]), cationic hydrophobic groups (—R$_1$—N—[(R$_2$)(R$_3$)(Hphob$_2$)]), and combinations of two or more thereof, either bonded thereto (for nucleophilic groups) or linked thereto via linking groups (for hydrophobic, cationic, and/or cationic hydrophobic groups). In certain preferred embodiments, the node structure consists only of carbon, hydrogen, and oxygen atoms from glyceryl remnant units. In certain preferred embodiments, the node structure consists only of carbon, hydrogen, and oxygen atoms from glyceryl remnant units and oxyalkyl units. In certain preferred embodiments, all glyceryl remnant units, and optional oxylalkyl units if any, of the node structure are contiguous. According to certain embodiments, the node structure has a ratio of carbon atoms to oxygen atoms (by number) that is from about 2.5 to about 4.5:1, preferably from about 2.5 to about 3.5:1, such as from about 2.6 to about 3.4:1, such as from about 2.8 to about 3.4:1.

Examples of suitable node structures are illustrated below in the description of certain specific examples of cationic polyglyceryl compounds. As one skilled in the art will readily appreciate, the polyglyceryl node structure includes a plurality of ether functional groups, and as such, the compounds may further be described as "polyethers."

As described above, the cationic polyglyceryl compounds of the present invention further comprise at least one cationic group and at least one hydrophobic moiety. A compound of the present invention may comprise any suitable combination of one or more cationic groups, hydrophobic groups, and/or cationic hydrophobic groups (i.e. a cationic group wherein a hydrophobic moiety constitutes a portion of the cationic group) such that the compound has both at least one cationic group and at least one hydrophobic moiety. For example, in certain embodiments, a compound of the present invention may comprise one cationic hydrophobic group alone (or optionally in combination with any additional number of separate cationic groups, cationic hydrophobic groups, or hydrophobic groups), or may comprise at least one cationic group (with or without hydrophobic moieties) and at least one hydrophobic group alone (or optionally in combination with any additional number of separate cationic groups, cationic hydrophobic groups, or hydrophobic groups).

Any suitable cationic group may be linked to the node structure via a linking group in a compound of the present invention. Suitable cationic groups may include groups bearing a positive charge, such as, for example, an amine, including a quarternary amine or a tertiary amine (in the latter case one of the R groups bonded to the nitrogen would be a hydrogen (H)). In a preferred embodiment, the cationic moiety is a quaternary amine. Examples of preferred quaternary amines include those illustrated by the structures —R$_1$—N—[(R$_2$)(R$_3$)(Hphob$_2$)] and —R$_4$—N—[(R$_5$)(R$_6$)(R$_7$)], as shown in Formula I, wherein R$_1$ and R$_4$ are independently selected linear, branched, saturated or unsaturated C$_1$ to C$_6$ hydrocarbon chains that may be optionally further substituted with nucleophilic functional groups such as —OH, —SH or —NH$_2$; R$_2$, R$_5$, R$_6$, and R$_7$ are independently selected C$_1$ to C$_4$ alkyl groups (CH$_3$ to C$_4$H$_9$) or hydrogen (H); R$_3$ is an independently selected C$_1$ to C$_4$ alkyl group (CH$_3$ to C$_4$H$_9$), hydrogen, or a hydrophobic moiety; and Hphob$_2$ is a hydrophobic moiety. Examples of preferred R$_1$ and R$_4$ groups include C$_1$ to C$_3$ linear alkyl groups or 2-hydroxypropyl. In certain preferred embodiments, R$_1$ and R$_4$ are CH$_2$CH(OH)CH$_2$—. Examples of preferred C$_1$ to C$_4$ alkyl groups include hydrogen, methyl, ethyl, propyl, isopropyl, butyl, tert-butyl, and isobutyl.

The relative amounts of cationic moieties and position on the polyglyceryl compound may vary. As such, both "b" and "c" in Formula I are each independently from zero to ten, more preferably from zero to 5, and more preferably from zero to 3, provided that the total number of cationic moieties per node structure, i.e. the sum of b and c, is from one to ten inclusive. In preferred embodiments, b is at least one. In certain preferred embodiments the sum of b and c is from one to 5, more preferably from one to 3, and more preferably from one to 2.

Serving to charge balance each cationic moiety is optional anionic counterions X$_1$ and/or X$_2$. Anionic counterions X$_1$ and X$_2$ are independent organic or inorganic cosmetically acceptable anions. Typical inorganic anions are halides, sulfates, phosphates, nitrates, and borates. Most preferred are halides, especially chloride. Another suitable organic anionic counterions include methosulfate, toluoyl suflate, acetate, citrate, taurate, glycolate, lactate, gluconate, and benzensulfonate, and the like.

Any suitable hydrophobic moieties (e.g. $Hphob_1$ and $Hphob_2$ in Formula I) may be incorporated in the compounds of the present invention. By "hydrophobic moiety," it is meant a nonpolar moiety that contains at least one of the following: (a) a carbon-carbon chain of at least six carbons in which none of the six carbons is a carbonyl carbon or has a hydrophilic moiety bonded directly to it; (b) three or more alkyl siloxy groups (—[Si(R)$_2$—O]—); and/or (c) three or more oxypropylene groups in sequence. A hydrophobic moiety may be, or include, linear, cyclic, aromatic, saturated or unsaturated groups. Preferred hydrophobic moieties include 6 or more carbon atoms, more preferably from 8 to 30 carbon atoms, even more preferably from 10 to 26 carbon atoms, and most preferably from 12 to 24 carbon atoms. Examples of hydrophobic moieties include linear or branched, saturated or unsaturated alkyl moieties, e.g. linear or branched, saturated or unsaturated $C_{10}$-$C_{30}$ alkyl, such as decyl, undecyl, dodecyl (lauryl), tridecyl, tetradecyl (myristyl), pentadecyl, hexadecyl (cetyl, palmityl), heptadecyl, heptadecenyl, hepta-8-decenyl, hepta-8,11-decenyl, octadecyl (stearyl), nonadecyl, eicosanyl, henicosen-12-yl, henicosanyl, docosanyl (behenyl), and the like as well as benzyl. Certain preferred hydrophobic moieties include heptadecyl, heptadecenyl, hepta-8-decenyl, hepta-8,11-decenyl and the like. Other examples of hydrophobic moieties include groups such as poly(oxypropylene), poly(oxybutylene), poly(dimethylsiloxane), and fluorinated hydrocarbon groups containing a carbon chain of at least six carbons in which none of the six carbons has a hydrophilic moiety bonded directly to it, and the like. Examples of certain preferred hydrophobic moieties for $Hphob_1$ are undecyl, pentadecyl heptadecenyl, and hepta-8-decenyl, and for $Hphob_2$ are dodecyl (lauryl), cocoalkyl, and stearyl.

The relative amounts of hydrophobic moieties and position on the polyglyceryl compound may vary. As such, both "a" and "b" in Formula I are each independently from zero to ten, more preferably from zero to 5 and more preferably from zero to 3 provided that the total number of hydrophobic moieties per node structure, i.e. the sum of a and b, is from one to ten inclusive. In preferred embodiments, b is at least one. In certain preferred embodiments the sum of a and b is from one to 5, more preferably from one to 3, and more preferably one to 2.

According to certain preferred embodiments, the compounds of the present invention are compounds of Formula I wherein the sum of a+b+c+d may be less than or equal to 5, or greater than 5. In such embodiments, if the sum of a+b+c+d is less than or equal to 5, then the quotient of a+b+c divided by a+b+c+d (a+b+c/a+b+c+d) is preferably greater than 0.33. Alternatively, if the sum of a+b+c+d is greater than 5, then the quotient a+b+c/a+b+c+d is from 0.04 to 0.9. In certain more preferred embodiments, if the sum of a+b+c+d is greater than 5, then the quotient a+b+c/a+b+c+d is from 0.04 to 0.7, more preferably 0.04 to 0.6.

The compounds of the present invention may have any suitable linking groups (e.g. $L_1$, $L_2$, and/or $L_3$ in Formula I) for linking cationic groups and/or hydrophobic groups to the node. By "linking to the node" it is meant that the cationic group and/or hydrophobic group is bonded to the node with only a linking group therebetween. Examples of suitable linking groups include functional moieties that when linked to at least two carbon atoms form ethers, esters, carbamates (urethanes), amides, ketones, or carbonates. That is, as will be understood by one of skill in the art, each linking group may be selected from: —O—, —OC(O)—, —OC(O)N(H)—, —C(O)N(H)—, —C(O)—, —OC(O)O—, and the like. Preferred linking groups include ether (—O—), and ester —(OC(O)—) linkages, more preferably ether linkages for linking groups $L_2$ and $L_3$ and ether or ester linkages for linking group $L_1$.

In certain embodiments, the linking group that are present (e.g. $L_1$, $L_2$, and/or $L_3$) are wholly or partially derived from a hydroxyl group of the polyglyceryl repeat units that were reacted in the process of making the cationic polyglyceryl compound/composition. For example, if a hydroxyl group present on a polyglyceryl is reacted with fatty acids under condensation reaction conditions, then the resulting node structure will be have hydrophobic moieties covalently linked thereto by $L_1$ groups that are ester functional groups (—OC(O)—). According to another embodiment, the various linking groups may be derived from a difunctional reagent. For example, if a hydroxyl group on the polyglyceryl is reacted with a diisocyanate, followed by reaction with a fatty alcohol, then the resulting Z will be substituted with hydrophobic moieties covalently linked to the node structure by $L_1$ groups that are carbamate (urethane) functional groups.

The cationic polyglyceryl compounds of the present invention may have any suitable nucleophilic groups bonded to the node structures. By nucleophilic groups, it is meant electron donating functional groups such as hydroxyl (—OH), amino (—NH$_2$), and thiol (—SH) groups. In a preferred embodiment each nucleophilic group is a hydroxyl group (—OH). The number of nucleophilic groups "d" directly bonded to the node structure is from 1 to about 21, preferably from 1 to about 16, and preferably from 1 to about 11.

While not intending to be limiting to any of the following structures, applicants provide herein specific examples of compounds within the scope of the invention to further illustrate compounds of Formula I, and compositions comprising such compounds. For example, in certain preferred embodiments a composition of the present invention may comprise a cationic polyglyceryl compound N-(2-hydroxypropyl)-N,N-dimethyllauryl-1-ammonium chloride decaglyceryl ether, the idealized structure for which is shown below:

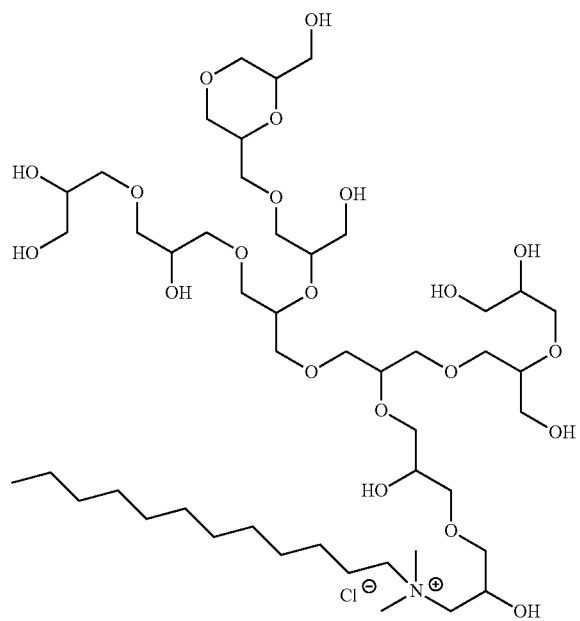 [SMILES: CCCCCCCCCCCC[N+](C)(C)CC(O)COCC(O)COC(COCC(CO)OCC(O)CO)COCC(COCC(O)COCC(O)CO)OC(CO)COCC1COCC(CO)O1 ; [Cl-]]

Wherein with reference to Formula I,
(a) Z, represented by the structure below, is a decaglyceryl remnant comprised of glyceryl remnant units [with a C/O ratio of 30/10=3]

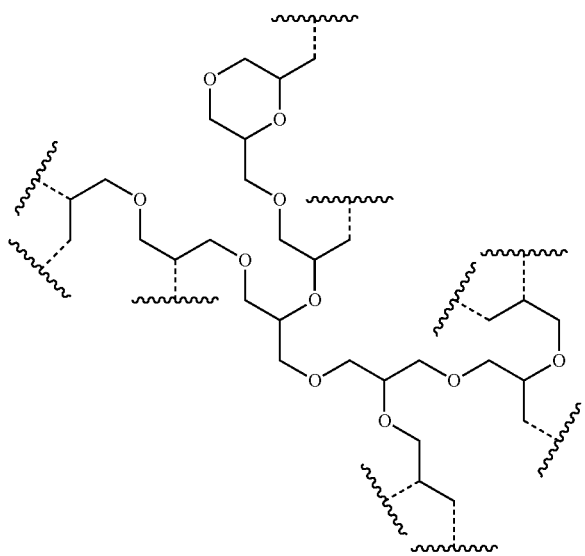

(b) d is the number of nucleophilic groups (—OH) directly attached to Z and is equal to 9
(c) $L_1$ is absent
(d) $Hphob_1$ is absent
(e) a is 0
(f) $L_2$ is an ether linking group which links Z to $R_1$
—O—
(g) $R_1$ is 2-hydroxypropyl

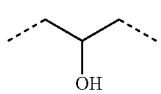

(h) N is a nitrogen species;

(i) $R_2$ is a methyl group
—$CH_3$
(j) $R_3$ is a methyl group
—$CH_3$
(k) $Hphob_2$ is a lauryl group

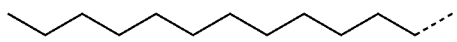

(l) $X_1$ is the counterion
$Cl^\ominus$
(m) b is 1 since there is 1 ($L_2$-$R_1$—N—[($R_2$)($R_3$)($Hphob_2$)]) per Z
(n) $L_3$ is absent
(o) $R_4$ is absent
(p) $R_5$ is absent
(q) $R_6$ is absent
(r) $R_7$ is absent
(s) $X_2$ is absent (t) c is 0 since there is 0 ($L_3$-$R_5$—N—[($R_6$)($R_7$)($R_8$)]) per Z;
(u) the sum of a and b is equal to 1
(v) and the sum of b and c is 1
(w) and the sum of a, b, and c is 1.

In certain preferred embodiments a composition of the present invention may comprise a cationic polyglyceryl compound (N-(2-hydroxypropyl)-N,N-dimethyllauryl-1-ammonium) (N-(2-hydroxypropyl)-N,N,N-trimethylpropan-1-ammonium) octaglyceryl ether, the idealized structure for which is shown below:

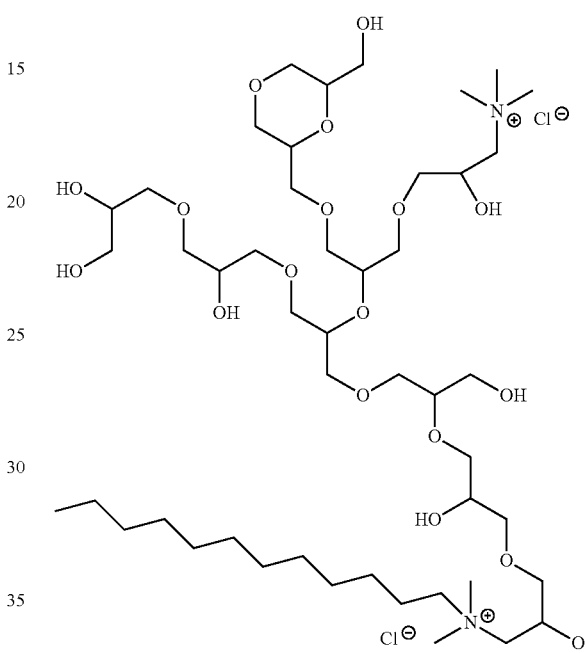

(a) Z, represented by the structure below, is a octaglyceryl remnant comprised of glyceryl remnant units [with a C/O ratio of 22/8=2.75]

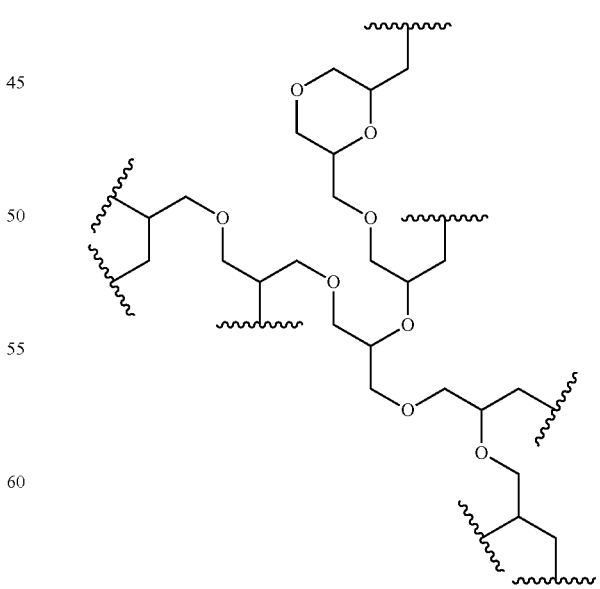

(b) d is the number of nucleophilic groups directly attached to Z and is equal to 6

(c) $L_1$ is absent
(d) $Hphob_1$ is absent
(e) a is 0 since there are no PG hydroxyls substituted with $(L_1\text{-}Hphob_1)$
(f) $L_2$ is an ether linking group which links Z to $R_1$
—O—
(g) $R_1$ is 2-hydroxypropyl

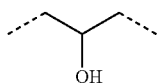

(h) N is a nitrogen species;

(i) $R_2$ is a methyl group
—$CH_3$
(j) $R_3$ is a methyl group
—$CH_3$
(k) $Hphob_2$ is a lauryl group

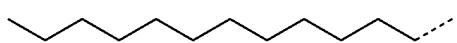

(l) $X_1$ is the counterion
$Cl^\ominus$ (m) b is 1 since there is 1 $(L_2\text{-}R_1\text{—N—}[(R_2)(R_3)(Hphob_2)])$ per Z
(n) $L_3$ is an ether linking group which links Z to $R_4$
—O—
(o) $R_4$ is 2-hydroxypropyl

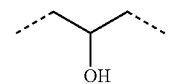

(p) $R_5$ is a methyl group
—$CH_3$
(q) $R_6$ is a methyl group
—$CH_3$
(r) $R_7$ is a methyl group
—$CH_3$
(s) $X_2$ is the counterion
$Cl^\ominus$
(t) c is 1 since there is on average 1 $(L_3\text{-}R_5\text{—N—}[(R_6)(R_7)(R_8)])$ per Z
(u) the sum of a and b is equal to 1
(v) and the sum of b and c is 2
(w) and the sum of a, b, and c is 2.

In certain preferred embodiments a composition of the present invention may comprise a cationic polyglyceryl compound (N-(2-hydroxypropyl)-N,N-dimethylcocoalkyl-1-ammonium) decaglyceryl monooleate ether, the idealized structure for which is shown below:

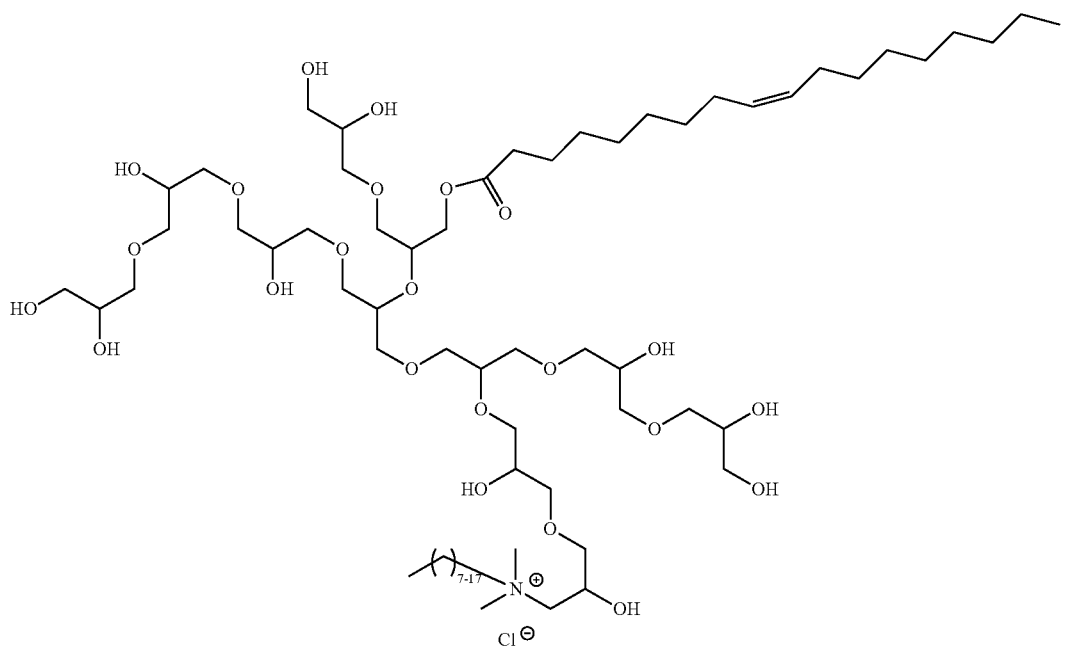

Wherein with reference to formula I,
(a) below, is a decaglyceryl remnant 10 remnant comprised of glyceryl remnant units [with a C/O ratio of 30/9=3.3]

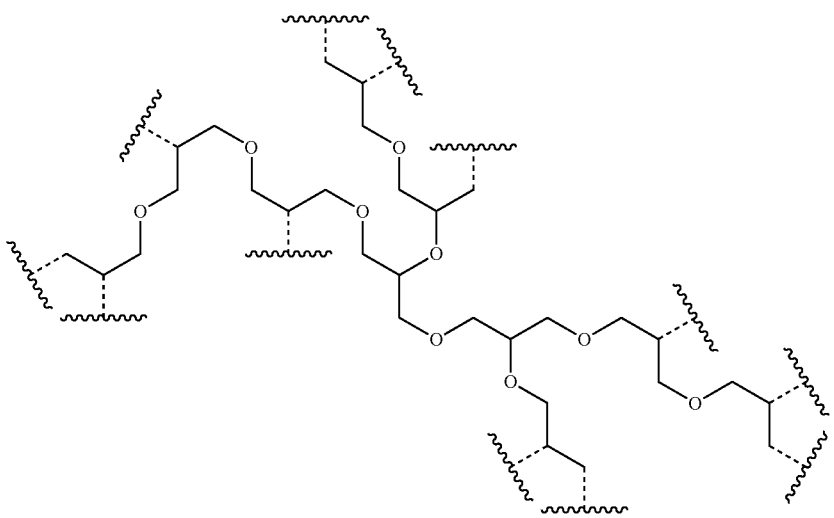

(b) d is the number of nucleophilic groups directly attached to Z and is equal to 10

(c) $L_1$ is an ester linkage

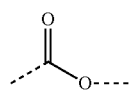

(d) Hphob$_1$ is 8-heptadecenyl

(e) a is 1 since there is 1 ($L_1$-Hphob$_1$) per Z (f) $L_2$ is an ether linking group which links Z to $R_1$

—O—

(g) $R_1$ is 2-hydroxypropyl

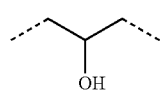

(h) N is a nitrogen species;

(i) $R_2$ is a methyl group

—CH$_3$ (j) $R_3$ is a methyl group

—CH$_3$ (k) Hphob$_2$ is cocoalkyl group which is known to those familiar in the art to be a distribution of saturated and unsaturated $C_8$-$C_{18}$ (based on the C chain distribution of coconut fatty acids from coconut oil)

(l) $X_1$ is the counterion

Cl$^{\ominus}$ (m) b is 1 since there is 1 ($L_2$-$R_1$—N—[($R_2$)($R_3$)(Hphob$_2$)]) per Z (n) $L_3$ is absent (o) $R_4$ is absent (p) $R_5$ is absent (q) $R_6$ is absent (r) $R_7$ is absent (s) $X_2$ is absent (t) c is 0 since there is on average 0 ($L_3$-$R_5$—N—[($R_6$)($R_7$)($R_8$)]) per Z (u) the sum of a and b is equal to 2

(v) and the sum of b and c is 1

(w) and the sum of a, b, and c is 2.

In certain preferred embodiments a composition of the present invention may comprise a cationic polyglyceryl compound (N-(2-hydroxypropyl)-N,N-dimethyllauryl-1-ammonium) (N-(2-hydroxypropyl)-N,N-trimethylpropan-1-ammonium) decaglyceryl monooleate ether, the idealized structure for which is shown below:

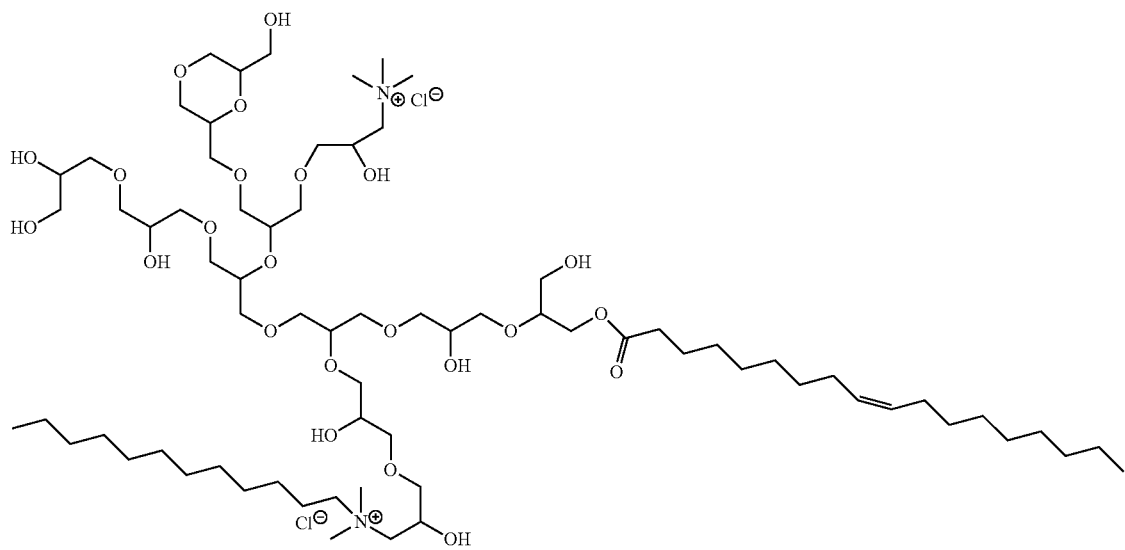 [SMILES: CCCCCCCC/C=C\CCCCCCCC(=O)OCC(CO)OCC(O)COCC(COCC(COCC(O)COCC(O)CO)OC(COCC(O)C[N+](C)(C)C)COCC1COCC(CO)O1)OCC(O)COCC(O)C[N+](C)(C)CCCCCCCCCCCC ; [Cl-] ; [Cl-]]

Wherein with reference to formula I, (a) Z, represented by the structure below, is a decaglyceryl remnant comprised of glyceryl remnant units

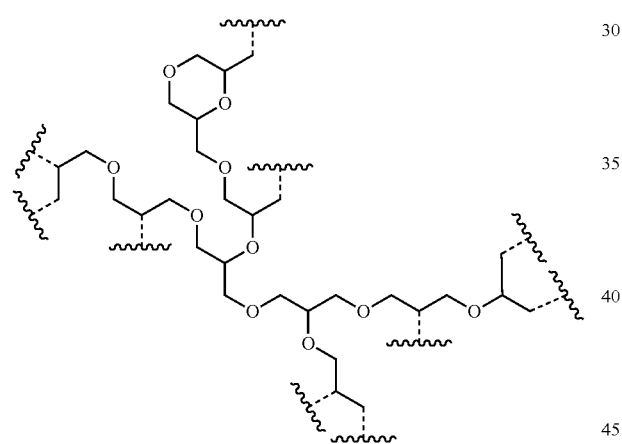

(b) d is the number of nucleophilic groups directly attached to Z and is equal to 7
(c) $L_1$ is an ester linkage

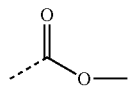

(d) Hphob$_1$ is 8-heptadecenyl

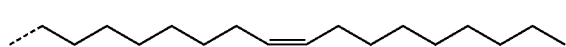

(e) a is 1 since there is 1 ($L_1$-Hphob$_1$) per Z
(f) $L_2$ is an ether linking group which links Z to $R_1$
—O—

(g) $R_1$ is 2-hydroxypropyl

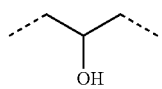

(h) N is a nitrogen species;

(i) $R_2$ is a methyl group
—CH$_3$
(j) $R_3$ is a methyl group
—CH$_3$
(k) Hphob$_2$ is cocoalkyl group which is known to those familiar in the art to be a distribution of saturated and unsaturated $C_8$-$C_{18}$

(l) $X_1$ is the counterion
Cl$^{\ominus}$
(m)$_b$ is 1 since there is on average 1 ($L_2$-$R_1$—N—[($R_2$)($R_3$)(Hphob$_2$)]) per Z
(n) $L_3$ is an ether linking group which links Z to $R_4$
—O—
(o) $R_4$ is 2-hydroxypropyl

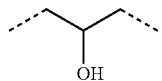

(p) $R_5$ is a methyl group
—CH$_3$ (q) $R_6$ is a methyl group
—$CH_3$
(r) $R_7$ is a methyl group
—$CH_3$
(s) $X_2$ is the counterion
$Cl^\ominus$
(t) c is 1 since there is on average 1 ($L_3$-$R_5$—N—[($R_6$)($R_7$)($R_8$)]) per Z
(u) the sum of a and b is equal to 2
(v) and the sum of b and c is 2
(w) and the sum of a, b, and c is 3.

In certain preferred embodiments a composition of the present invention may comprise a cationic polyglyceryl compound (N-(2-hydroxypropyl)-N,N,N-trimethylpropan-1-ammonium) decaglyceryl monooleate ether, the idealized structure for which is shown below:

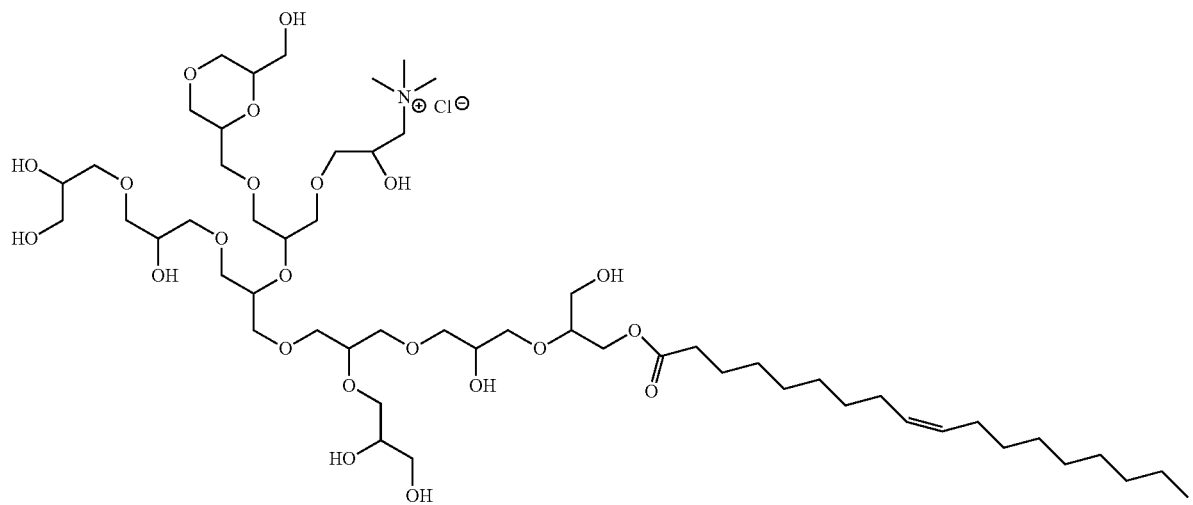

Wherein with reference to formula I,
(a) Z, represented by the structure below, is a decaglyceryl remnant comprised of glyceryl remnant units[with a C/O ratio of 30/10=3]

(b)
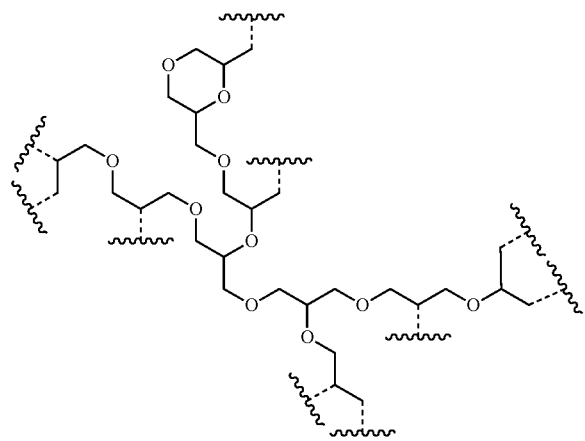

(c) d is the number of nucleophilic groups directly attached to Z and is equal to 10

(d) $L_1$ is an ester linkage

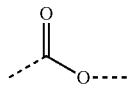

(e) Hphob$_1$ is 8-heptadecenyl

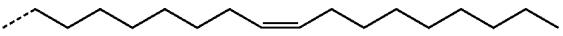

(f) a is 1 since there is on average 1 ($L_1$-Hphob$_1$) per Z
(g) $L_2$ is absent
(h) $R_1$ is absent
(i) N is a nitrogen species;

(j) $R_2$ is absent
(k) $R_3$ is absent
(l) Hphob$_2$ is absent
(m) $X_1$ is absent
(n) b is 1 since there is 1 ($L_2$-$R_1$—N—[($R_2$)($R_3$)(Hphob$_2$)]) per Z
(o) $L_3$ is an ether linking group which links Z to $R_4$
—O—
(p) $R_4$ is 2-hydroxypropyl

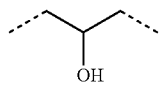

(q) $R_5$ is a methyl group
—$CH_3$
(r) $R_6$ is a methyl group
—$CH_3$ (s) $R_7$ is a methyl group
—$CH_3$
(t) $X_2$ is the counterion
$Cl^\ominus$
(u) c is 1 since there is on average X ($L_3$-$R_5$—N—[($R_6$)($R_7$)($R_8$)]) per Z
(v) the sum of a and b is equal to 1
(w) and the sum of b and c is 1
(x) and the sum of a, b, and c is 2.

Methods of Making Cationic Polyglyceryl Compounds and Compositions

The cationic polyglyceryl compounds and compositions of this invention may be synthesized by various synthetic routes including but not limited to the reaction of nitrogen-containing compounds with polyglycerol (PG) or polyglyceryl esters (PGE). The PG or PGE may be any of various commercially available varieties. Illustrative examples of PG and PGE starting materials include but are not limited to polyglycerols (such as Natrulon® H-10 from Lonza PLC of Basel, Switzerland) and polyglyceryl esters (such as Polyaldo® 10-1-O KFG and Polyaldo® 10-1-L from Lonza PLC) and polyglyceryl ethers (such as Polyglycerin Ether ML10 from Daicel Chemical Industries, LTD. of Hiroshima, Japan)

A schematic example of a polyglycerol having 11 glyceryl repeat units ($DP_{OH}$=11), having $L_{1,3}$, $L_{1,4}$, D, $T_{1,3}$, and $T_{1,2}$ structural units is shown below. The three carbons which comprise each class of structural unit have been labeled to provide a detailed example.

Commercially available halohydrins include Quab® 188, 342, 360, and 426 which correspond to 3-chloro-2-hydroxypropyl-alkyl-dimethylammonium chloride (CHADAC) where the alkyl groups are respectively methyl, lauryl, cocoalkyl, and stearyl. A commercially available epoxy reagent includes Quab® 151 (2,3-epoxypropyltrimethylammonium chloride). Quab® halohydrins are commercially available from SKW QUAB Chemicals, Inc of Theodore, Ala.

The Quab® quaternized halohydrin may be reacted with PG or PGEs in the presence of a base catalyst. Accordingly, in one embodiment, the method of making the C-PG includes the reaction of a PG with a quaternized halohydrin in the presence of a base catalyst. Suitable catalysts include alkali metal, particularly sodium or potassium, bases, e.g. hydroxides, particularly NaOH or KOH, carbonates, particularly $K_2CO_3$ or $Na_2CO_3$, bicarbonates, particularly $KHCO_3$ or $NaHCO_3$ and tertiary amines, particularly tertiary amines including at least one tertiary nitrogen atom in a ring system, such as 1,8-diazabicyclo[5.4.0]undec-7-ene (DBU), 1,4-diazabicyclo[2.2.2]octane (DABCO), 4-(dimethylamino)pyridine (DMAP), 7-methyl-1,5,7-triazabicyclo[4.4.0]dec-5-ene (MTBD), quinuclidine, pyrrocoline, and similar materials In a preferred embodiment, an alkali metal hydroxide is utilized as a base catalyst. Suitable alkali metal hydroxides include sodium hydroxide, potassium hydroxide, calcium hydroxide, barium hydroxide, cesium hydroxide, lithium

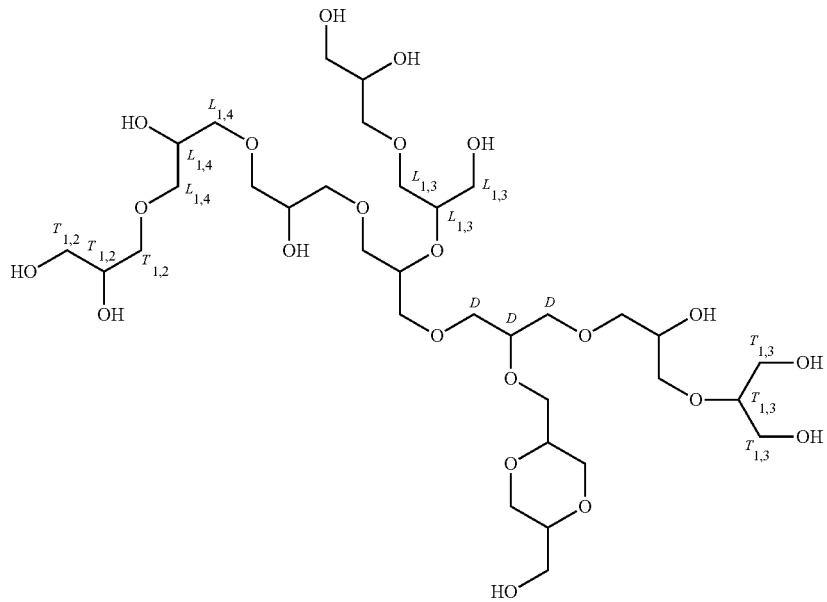 [SMILES: OCC(O)COCC(O)COCC(O)COCC(COCC(COCC(O)COC(CO)CO)OCC1COC(CO)CO1)OC(CO)COCC(O)CO]

The nitrogen containing reactants may be quaternized either before or after conjugation to the PG/PGE. Illustrative cationization reagents include epoxy and halohydrin derivatives containing an amine group. Generalized structures of suitable quaternized starting reagents are shown below:

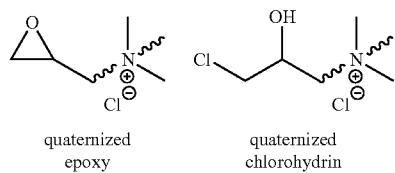

quaternized epoxy    quaternized chlorohydrin hydroxide, rubidium hydroxide, and strontium hydroxide. Sodium, potassium, and calcium hydroxide are preferred due to the lower cost and availability. Typically, the molar ratio of halohydrin to alkali metal hydroxide is 1:0.5 to 1:50, typically 1:1 to 1:4, though more usually from 1:1 to 1:3, desirably 1:1.03 to 1:2 and particularly from 1:1.03 to 1:1.5. The desired molar ratio of halohydrin to alkali metal hydroxide may be increased or decreased depending on the concentration of water in solution. Typically, the molar ratio of epoxide to alkali metal hydroxide is 1:0.01 to 1:50, typically 1:0.01 to 1:10, though more usually from 1:0.01 to 1:3, desirably 1:0.01 to 1:2 and particularly from 1:0.01 to 1:1.

In addition to the compounds of the invention, typical synthesis reactions may generate by-products such as 2,3- propanediol-trialkylammonium chloride which is produced from the side reaction of water and the corresponding 3-chloro-2-hydroxytrialkylammonium chloride or hydrolysis of 2,3-epoxypropyltrimethylammonium chloride. Generally, a minimum amount of water is required for the cationization reaction to proceed. However, increasing the water content above this amount may lead to an increase in side products. However, those skilled in the art will note that reaction conditions which minimize side products should be employed. While removal is not critical, the diol side products may be removed via any of a variety of conventional separation processes including, for example, precipitation, column chromatography, and solvent extraction.

Alternatively, C-PGs can be formed by reacting PGs or PGEs with halohydrin alcohols (i.e. 3-chloro-2-hydroxypropanediol) under acidic conditions to produce a halohydrin PG/PGE intermediate. Subsequently, the product is reacted with an alkali metal hydroxide to yield a glycidyl PG/PGE which may be further reacted with an aminoalkyl ammonium or alkyl amine to yield a C-PG. If an alkyl amine is employed, an additional quaternization step (i.e. reaction with halomethane) may be employed to yield the desired quaternary amine.

Alternatively, C-PGs can be formed by reacting PGs or PGEs with epichlorohydrins under basic conditions to produce an epoxy-functional PG/PGE. Subseqently, the epoxy-functional PG/PGE may be reacted with a tertiary amine to yield the desired C-PG. If a secondary amine is employed in place of the tertiary amine, an addition quaternization step (i.e. reaction with iodomethane) may be employed to yield a quaternary amine.

In addition, adjuvants may be used during different synthetic steps. Typical adjuvants include but are not limited to: base neutralizers such as citric, acetic, tartaric, hydrochloric, and sulfuric acids.

The synthetic reactions will be generally be carried out in a batch mode, typically by mixing the reagents in a suitable vessel and allowing them to react, usually under stirring for a suitable time. Fresh reagent and/or catalyst may be added occasionally, at multiple intervals or continuously during the reaction (semi-batch operation). It is also possible to use continuous or semicontinuous reaction modes if desired.

As the PGs or PGEs is modified with cationization reactants, the solubility of the product may change based on the hydrophilicity/hydrophobicity of the cationization reactant. Thus, the intermediates and the products may have a distinct phase nature from the starting reaction mixture. Reaction between components (generally) in different phases will be slower than when they are in one phase. The degree of compatibility of the intermediates may influence the relative speed of reaction and thus influence the distribution of cationic functionalization among PG/PGEs. In some cases, a single phase liquid system will not form, giving rise to two different reaction products (one from each phase) that may be separated and utilized accordingly. In these cases, the reaction parameters may be adjusted accordingly to favor the formation of the desired product and minimize formation of the accompanying by product. For example, in a two-phase reaction product resulting from the reaction of CHADAC with PG-10, one phase may comprise a C-PG with a high degree of alkyl dimethylammonium functionalization, whereas the second phase may comprise a C-PG with a low degree of alkyl dimethylammonium functionalization. The two phases may be separated and collected via any of a variety of conventional separation processes including, for example, decanting, fractionation, centrifugation, and/or solvent extraction.

Typically, the reactions to make the compounds of the invention can be carried out without the need for a solvent or diluent, particularly as this will avoid any problem in isolating the desired product. However, if desired, the physical immiscibility of the starting materials may be avoided by the use of suitable inert reaction medium, solvent or diluent; however, the reaction is preferably conducted in the bulk or water.

Suitable solvents are liquids which remain thermally stable throughout the course of the reaction. Suitable examples of solvents/diluents include water, and polar aprotic solvents.

Solvent and/or diluent may be included with the resulting cationic polyglyceryl composition, either by leaving reaction solvent/diluent in the product or by subsequent addition, to reduce product viscosity for transport, storage and/or subsequent use. Typically such solvents/diluents will be used in amounts to give formulations having from 50 to 90, more usually 60 to 80 and particularly about 70%, by weight of the product.

A heating step during the reaction may be employed. During this step the temperature may be room temperature to superambient, such as from 25° C. to at least 150° C. and more usually at least 40° C. up to 90° C., with the range 65 to 85° C. being generally suitable.

Typically, the reagents used to make the compounds of the invention remain liquids of low vapor pressure at reaction temperatures, so the reaction can be conveniently carried out at ambient pressure though moderately superambient pressure may be used if desired. It is unlikely that it will be desirable to use subambient pressure, but by choosing suitable involatile reagents it may be possible to carry the reaction out at moderately subambient pressure.

In certain reaction steps it may be preferred to apply subambient pressure (i.e. vacuum) to drive the reaction to completion and to remove volatile side products. It may also be preferential to apply subambient pressure to the reactants prior to the reaction for degassing purposes.

To help avoid excessive color generation, the synthesis reactions will usually be carried out in a largely oxygen free atmosphere, e.g. in a nitrogen atmosphere (e.g., using a nitrogen blanket or sparge). Other inert gases may be utilized such as argon. For larger scale production, nitrogen blanketing may be less necessary and perhaps omitted.

Another way of reducing product color is to include particulate carbon, particularly so-called "activated carbon", or a bleaching earth, e.g. diatomaceous earth, in the reaction to absorb colored side products. When used, the amount of carbon will typically be from 0.5 to 2.5 weight % of the total reagents. Of course, this carbon or bleaching earth will generally be removed e.g. by filtration, before the products are included in end use formulations. Activated carbon and a reducing agent may be used together in the reaction if desired. Further color improvement can be achieved by treatment of the reaction product with particulate carbon, particularly activated carbon, or bleaching earth, typically at from 0.5 to 2.5 weight % of the product.

According to certain embodiments of the invention, cationic polyglyceryl compositions are used in personal care compositions. The personal care composition may comprise, consist of, or consist essentially of a base and the cationic polyglyceryl composition. The base comprises water, surfactant, and optionally, any of various ingredients typically used in personal care products.

Any amounts of cationic polyglyceryl composition suitable to provide an "effective managing amount" where this term herein means an amount of cationic polyglyceryl composition to provide a composition with personal care utility. The effective managing amount typically ranges from 0.005 to about 10 weight percent, and more preferably from about 0.01 to 7 weight percent, and most preferably from about 0.05 to 5 weight percent.

According to certain embodiments of the invention, the cationic polyglyceryl composition is used in amount suitable to provide enhanced humectancy, enhanced conditioning or anti-fizz properties, enhanced foam properties, enhanced viscosity, enhanced, and or combinations thereof.

According to certain embodiments of the invention the cationic polyglyceryl composition is used in amount suitable to provide enhanced foam properties. For example, the cationic polyglyceryl composition may be included in an amount sufficient such that when the personal care composition is tested according to the Foam Test as described below, the personal care composition has a Foam Volume$_{max}$ of at least about 10 mL, preferably at least about 100 mL, more preferably at least about 200 mL, more preferably at least about 300 mL, more preferably at least about 500 mL, and most preferably at least about 700 mL. According to other embodiments, the cationic polyglyceryl composition may be included in an amount sufficient such that when the personal care composition is tested according to the Foam Test as described below, the personal care composition has a % foam retention of at least about 50%, preferably at least about 75%, more preferable at least about 90%.

According to certain embodiments of the invention the cationic polyglyceryl composition is used in amount suitable to provide enhanced viscosity. For example, the cationic polyglyceryl composition may be included in an amount sufficient such that when the personal care composition is tested according to the Zero Shear Viscosity Test as described below, the personal care composition has a Relative Viscosity of at least about 1.5, more preferably at least about 2, more preferably at least about 3, more preferably at least about 5, more preferably at least about 10. In certain preferred embodiments, the personal care compositions of the present invention comprise a sufficient amount of cationic polyglyceryl composition to achieve a Relative Viscosity of at least about 2, preferably about 5, more preferably about 10.

According to certain embodiments of the invention the cationic polyglyceryl composition is used in an amount suitable to provide enhanced conditioning and/or anti-fizz properties. For example, the cationic polyglyceryl composition may be included in an amount sufficient such that when the personal care composition is tested according to the Conditioning Test as described below, the personal care composition has an Average Comb Force of less than about 170 grams-force (gf), preferably less than about 165 gf, more preferably less than about 160 gf. In certain preferred embodiments, the personal care compositions of the present invention comprise a sufficient amount of cationic polyglyceryl composition to achieve a Average Comb Force of less than about 170 gf, preferably less than about 165 gf, more preferably less than about 160 gf, and are substantially free of other known humectants.

According to other embodiments, the cationic polyglyceryl composition may be included in an amount sufficient such that when the personal care composition is tested according to the Anti-Frizz Test as described below, the personal care composition has a % Frizz of less than about 20%, preferably less than about 15%, more preferably less than about 12%. In certain preferred embodiments, the personal care compositions of the present invention comprise a sufficient amount of cationic polyglyceryl composition to achieve a % Frizz of less than about 20%, preferably less than about 15%, more preferably less than about 12, and are substantially free of other known humectants.

According to certain embodiments of the invention the cationic polyglyceryl composition is used in amount suitable to provide enhanced humectancy. For example, the cationic polyglyceryl composition may be included in an amount sufficient such that when the sample composition is tested according to the Water Sorption Test as described below, the cationic polyglyceryl composition has a % $\Delta Mass_{50\ RH\ sorp}$ of greater than about 8, preferably greater than about 8.5, more preferably greater than about 10, even more preferably greater than about 12. In certain preferred embodiments, the personal care compositions of the present invention comprise a sufficient amount of cationic polyglyceryl composition to achieve a % $\Delta Mass_{50\ RH\ sorp}$ of greater than about 8, preferably greater than about 8.5, more preferably greater than about 10, even more preferably greater than about 12, and are substantially free of other known humectants.

In certain embodiments, the compositions useful in the present invention may include any variety of additional surfactants. The surfactants may be anionic, zwitterionic (i.e. amphoteric or betaine), nonionic, or cationic, examples of which are detailed below. Where applicable, chemicals are specified according to their International Nomenclature of Cosmetic Ingredients (INCI) names.

According to certain embodiments, suitable anionic surfactants include those selected from the following classes of surfactants: alkyl sulfates, alkyl ether sulfates, alkyl monoglyceryl ether sulfates, alkyl sulfonates, alkylaryl sulfonates, alkyl sulfosuccinates, alkyl ether sulfosuccinates, alkyl sulfosuccinamates, alkyl amidosulfosuccinates, alkyl carboxylates, alkyl amidoethercarboxylates, alkyl succinates, fatty acyl sarcosinates, fatty acyl amino acids, fatty acyl taurates, fatty alkyl sulfoacetates, alkyl phosphates, and mixtures of two or more thereof. Examples of certain preferred anionic surfactants include:

Alkyl sulfates

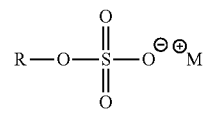

where R=$C_8$-$C_{24}$ alkyl (linear or branched, saturated or unsaturated) or mixtures thereof and $M^+$=monovalent cation. Examples include Sodium Lauryl Sulfate (R=$C_{12}$ alkyl, $M^+$=$Na^+$), Ammonium Lauryl Sulfate (R=$C_{12}$ alkyl, $M^+$=$NH_3^+$), and Sodium Coco-Sulfate (R=coconut alkyl, $M^+$=$Na^+$);

Alkyl ether sulfates

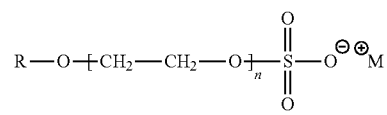

where R=$C_8$-$C_{24}$ alkyl (linear or branched, saturated or unsaturated) or mixtures thereof, n=1-12, and $M^+$=monovalent cation. Examples include Sodium Laureth Sulfate (R=$C_{12}$ alkyl, $M^+$=$Na^+$, n=1-3), Ammonium Laureth Sulfate (R=$C_{12}$ alkyl, $M^+$=$NH_3^+$, n=1-3), and Sodium Trideceth Sulfate (R=$C_{13}$ alkyl, $M^+$=$Na^+$, n=1-4);

Alkyl monoglyceride sulfates

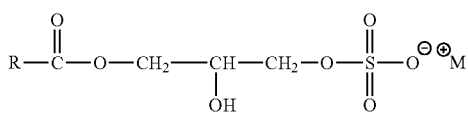

where R=$C_8$-$C_{24}$ alkyl (linear or branched, saturated or unsaturated) or mixtures thereof and $M^+$=monovalent cation. Examples include Sodium Cocomonoglyceride Sulfate (RCO=coco acyl, $M^+$=$Na^+$) and Ammonium Cocomonoglyceride Sulfate (RCO=coco acyl, $M^+$=$NH_3^+$);

Alkyl carboxylates

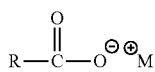

where R=$C_8$-$C_{24}$ alkyl (linear or branched, saturated or unsaturated) or mixtures thereof and $M^+$=monovalent cation. Examples include Sodium Laurate (R=$C_{11}H_{23}$, $M^+$=$Na^+$) and Potassium Myristate (R=$C_{13}H_{27}$, $M^+$=$K^+$);

Alkyl ether carboxylates

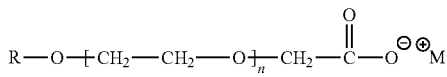

where R=$C_8$-$C_{24}$ alkyl (linear or branched, saturated or unsaturated) or mixtures thereof, n=1-20, and $M^+$=monovalent cation. Examples include Sodium Laureth-13 Carboxylate (R=$C_{12}$ alkyl, $M^+$=$Na^+$, n=13), and Sodium Laureth-3 Carboxylate (R=$C_{12}$ alkyl, $M^+$=$Na^+$, n=3);

Alpha olefin sulfonates prepared by sulfonation of long chain alpha olefins. Alpha olefin sulfonates consist of mixtures of alkene sulfonates,

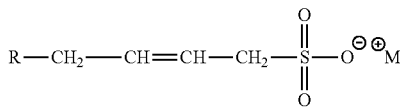

where R=$C_8$-$C_{18}$ alkyl or mixtures thereof and $M^+$=monovalent cation, and hydroxyalkyl sulfonates,

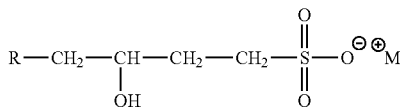

where R=$C_4$-$C_{18}$ alkyl or mixtures thereof and $M^+$=monovalent cation. Examples include Sodium C12-14 Olefin Sulfonate (R=$C_8$-$C_{10}$ alkyl, $M^+$=$Na^+$) and Sodium C14-16 Olefin Sulfonate (R=$C_{10}$-$C_{12}$ alkyl, $M^+$=$Na^+$);

Alkyl sulfonates:

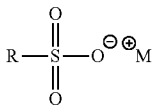

where R=$C_8$-$C_{24}$ alkyl (linear or branched, saturated or unsaturated) or mixtures thereof and $M^+$=monovalent cation. Examples include Sodium C13-17 Alkane Sulfonate (R=$C_{13}$-$C_{17}$ alkyl, $M^+$=$Na^+$) and Sodium C14-17 Alkyl Sec Sulfonate (R=$C_{14}$-$C_{17}$ alkyl, $M^+$=$Na^+$);

Alkylaryl sulfonates

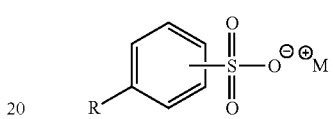

where R=$C_6$-$C_{18}$ alkyl (linear or branched, saturated or unsaturated) or mixtures thereof and $M^+$=monovalent cation. Examples include Sodium Deceylbenzenesulfonate (R=$C_{10}$ alkyl, $M^+$=$Na^+$) and Ammonium Dodecylbenzensulfonate (R=$C_{12}$ alkyl, $M^+$=$NH_3^+$);

Alkyl glyceryl ether sulfonates:

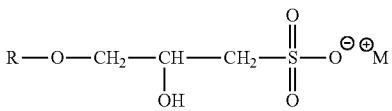

where R=$C_8$-$C_{24}$ alkyl (linear or branched, saturated or unsaturated) or mixtures thereof and $M^+$=monovalent cation, such as Sodium Cocoglyceryl Ether Sulfonate (R=coco alkyl, $M^+$=$Na^+$);

Alkyl sulfosuccinates

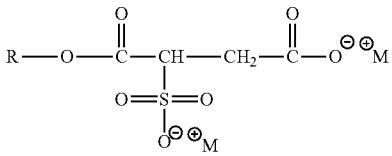

Where R=$C_8$-$C_{20}$ alkyl (linear or branched, saturated or unsaturated) or mixtures thereof and $M^+$=monovalent cation, such as Disodium Lauryl Sulfosuccinate (R=lauryl, $M^+$=$Na^+$).

Alkyl ether sulfosuccinates

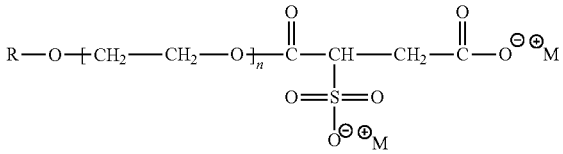

Where R=$C_8$-$C_{20}$ alkyl (linear or branched, saturated or unsaturated) or mixtures thereof, n=1-12, and $M^+$=monovalent cation, such as Disodium Laureth Sulfosuccinate (R=lauryl, n=1-4, and $M^+$=$Na^+$)

Dialkyl sulfosuccinates

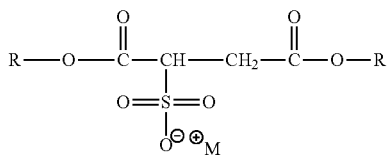

Where R=$C_6$-$C_{20}$ alkyl (linear or branched, saturated or unsaturated) or mixtures thereof and $M^+$=monovalent cation, such as Diethylhexyl Sodium Sulfosuccinate (R=2-ethylhexyl, $M^+$=$Na^+$).

Alkylamidoalkyl sulfosuccinates

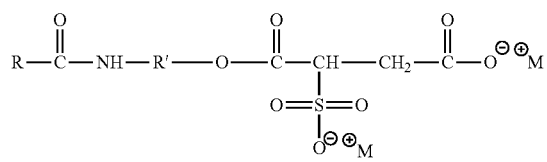

Where R=$C_8$-$C_{20}$ alkyl (linear or branched, saturated or unsaturated) or mixtures thereof, R'=$C_2$-$C_4$ alkyl (linear or branched), and $M^+$=monovalent cation, such as Disodium Cocamido MIPA-Sulfosuccinate (RCO=coco acyl, R'=isopropyl, $M^+$=$Na^+$).

Alkyl sulfosuccinamates

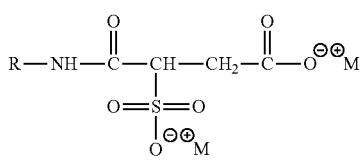

Where R=$C_8$-$C_{20}$ alkyl (linear or branched, saturated or unsaturated) or mixtures thereof and $M^+$=monovalent cation, such as Disodium Stearyl Sulfosuccinamate (R=stearyl, $C_{18}H_{37}$, $M^+$=$Na^+$).

α-Sulfo fatty acid esters

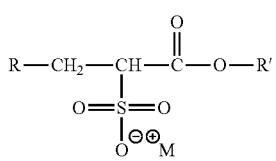

Where R=$C_6$-$C_{16}$ alkyl (linear or branched, saturated or unsaturated) or mixtures thereof, R'=$C_1$-$C_4$ alkyl, and $M^+$=monovalent cation, such as Sodium Methyl 2-Sulfolaurate (R=$C_{10}H_{21}$, R'=methyl, $CH_3$, and $M^+$=$Na^+$).

α-Sulfo fatty acid salts

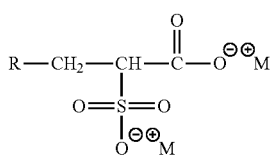

Where R=$C_6$-$C_{16}$ alkyl (linear or branched, saturated or unsaturated) or mixtures thereof, $M^+$=monovalent cation, such as Disodium 2-Sulfolaurate (R=$C_{10}H_{21}$, $M^+$=$Na^+$).

Alkyl sulfoacetates

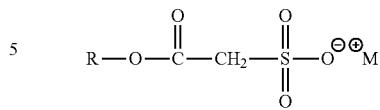

Where R=$C_8$-$C_{18}$ alkyl (linear or branched, saturated or unsaturated) or mixtures thereof, $M^+$=monovalent cation, such as Sodium Lauryl Sulfoacetate (R=lauryl, $C_{12}H_{25}$, $M^+$=$Na^+$).

Acyl isethionates

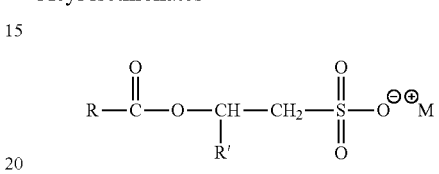

Where RCO=$C_8$-$C_{20}$ acyl (linear or branched, saturated or unsaturated) or mixtures thereof, R'=H or $CH_3$, $M^+$=monovalent cation, such as Sodium Cocoyl Isethionate (RCO=coco acyl, R'=H, $M^+$=$Na^+$) and Sodium Lauroyl Methyl Isethionate (RCO=lauroyl, R'=$CH_3$, $M^+$=$Na^+$).

Acyl lactylates

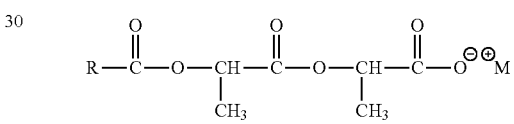

Where RCO=$C_8$-$C_{20}$ acyl (linear or branched, saturated or unsaturated) or mixtures thereof, $M^+$=monovalent cation, such as Sodium Lauroyl Lactylate (RCO=lauroyl, $M^+$=$Na^+$).

Acyl glycinates and acyl sarcosinates

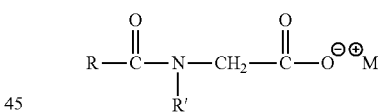

Where RCO=$C_8$-$C_{20}$ acyl (linear or branched, saturated or unsaturated) or mixtures thereof, R'=H (glycinate) or $CH_3$ (sarcosinate), $M^+$=monovalent cation, such as Sodium Cocoyl Glycinate (RCO=coco acyl, R'=H, $M^+$=$Na^+$), Ammonium Cocoyl Sarcosinate (RCO=coco acyl, R'=$CH_3$, $M^+$=$NH_4^+$) and Sodium Lauroyl Sarcosinate (RCO=lauroyl, R'=$CH_3$, $M^+$=$Na^+$).

Acyl glutamates

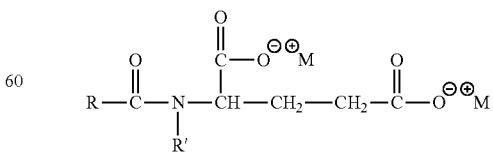

Where RCO=$C_8$-$C_{20}$ acyl (linear or branched, saturated or unsaturated) or mixtures thereof, R'=H or $CH_3$, $M^+$=monovalent cation, such as Disodium Cocoyl Glutamate (RCO=coco acyl, R'=H, M⁺=Na⁺) and Disodium Lauroyl Glutamate (RCO=lauroyl, R'=H, M⁺=Na⁺).
Acyl aspartates

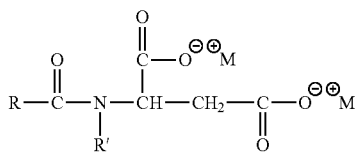

Where RCO=$C_8$-$C_{20}$ acyl (linear or branched, saturated or unsaturated) or mixtures thereof, R'=H or $CH_3$, M⁺=monovalent cation, such as Disodium N-Lauroyl Aspartate (RCO=lauroyl, R'=H, M⁺=Na⁺).
Acyl taurates

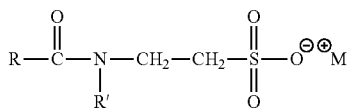

Where RCO=$C_6$-$C_{20}$ acyl (linear or branched, saturated or unsaturated) or mixtures thereof, R'=H or $CH_3$, M⁺=monovalent cation, such as Disodium Cocoyl Glutamate (RCO=coco acyl, R'=H, M⁺=Na⁺) and Disodium Lauroyl Glutamate (RCO=lauroyl, R'=H, M⁺=Na⁺).
Alkyl phosphates

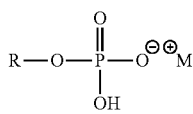

Where R=$C_6$-$C_{20}$ alkyl (linear or branched, saturated or unsaturated) or mixtures thereof and M⁺=monovalent cation, such as Potassium Lauryl Phosphate (R=lauryl, $C_{12}H_{25}$, M⁺=K⁺) and Potassium C12-13 Alkyl Phosphate (R=$C_{12}$-$C_{13}$ alkyl, M⁺=K⁺)

Anionic derivatives of alkyl polyglucosides (APGs), including: Sodium Lauryl Glucoside Carboxylate, Disodium Coco-Glucoside Citrate, Sodium Coco-Glucoside Tartrate, Disodium Coco-Glucoside Sulfosuccinate, Sodium Cocoglucosides Hydroxypropylsulfonate, Sodium Decylglucosides Hydroxypropylsulfonate, Sodium Laurylglucosides Hydroxypropylsulfonate, Sodium Hydroxypropylsulfonate Cocoglucoside Crosspolymer, Sodium Hydroxypropylsulfonate Decylglucoside Crosspolymer, Sodium Hydroxypropylsulfonate Laurylglucoside Crosspolymer; and anionic polymeric APG derivatives, such as those described in O'Lenick, U.S. Pat. Nos. 7,507,399; 7,375,064; and 7,335,627, and combinations of two or more thereof, and the like.

Any of a variety of amphoteric surfactants are suitable for use in the present invention. As used herein, the term "amphoteric" shall mean: 1) molecules that contain both acidic and basic sites such as, for example, an amino acid containing both amino (basic) and acid (e.g., carboxylic acid, acidic) functional groups; or 2) zwitterionic molecules which possess both positive and negative charges within the same molecule. The charges of the latter may be either dependent on or independent of the pH of the composition. Examples of zwitterionic materials include, but are not limited to, alkyl betaines and alkylamidoalkyl betaines. The amphoteric surfactants are disclosed herein with a counterion. One skilled in the art would readily recognize that under the pH conditions of the compositions of the present invention, the amphoteric surfactants are either electrically neutral by virtue of having balancing positive and negative charges, or they have counter ions such as alkali metal, alkaline earth, or ammonium counter ions. Examples of amphoteric surfactants suitable for use in the present invention include, but are not limited to, amphocarboxylates such as alkylamphoacetates (mono or di); alkyl betaines; alkylamidoalkyl betaines; alkylamidoalkyl sultaines; alkylamphophosphates; phosphorylated imidazolines such as phosphobetaines and pyrophosphobetaines; carboxyalkyl alkyl polyamines; alkylimino-dipropionates; alkylamphoglycinates (mono or di); alkylamphoproprionates (mono or di),); N-alkyl β-aminoproprionic acids; alkylpolyamino carboxylates; and mixtures thereof. Specific examples include:
Alkyl betaines

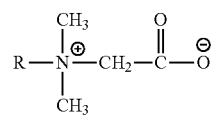

where R=$C_8$-$C_{24}$ alkyl (saturated or unsaturated) or mixtures thereof. Examples include Coco-Betaine (R=coco alkyl), Lauryl Betaine (R=lauryl, $C_{12}H_{25}$), and Oleyl Betaine (R=oleyl, $C_{18}H_{35}$).
Alkyl hydroxysultaines

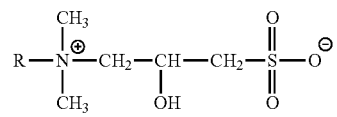

where R=$C_8$-$C_{24}$ alkyl (saturated or unsaturated) or mixture thereof. Examples include Coco-Hydroxysultaine (R=coco alkyl) and Lauryl Hydroxysultaine (R=lauryl, $C_{12}H_{25}$).
Alkyl sultaines

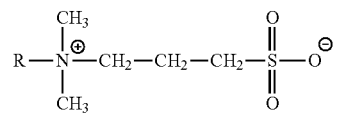

where R=$C_8$-$C_{24}$ alkyl (saturated or unsaturated) or mixture thereof. Examples include Lauryl Sultaine (R=lauryl, $C_{12}H_{25}$) and Coco-Sultaine (R=coco alkyl).
Alkylamidoalkyl betaines

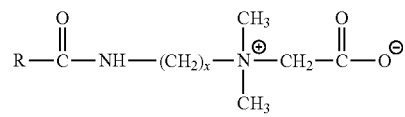

where RCO=$C_6$-$C_{24}$ acyl (saturated or unsaturated) or mixtures thereof and x=1-4. Examples include Cocamidoethyl Betaine (RCO=coco acyl, x=2), Cocamidopropyl Betaine (RCO=coco acyl, x=3), Lauramidopropyl Betaine (RCO=lauroyl, and x=3), Myristamidopropyl Betaine (RCO=myristoyl, and x=3), Soyamidopropyl Betaine (R=soy acyl, x=3), and Oleamidopropyl Betaine (RCO=oleoyl, and x=3).

Alkylamidoalkyl hydroxysultaines

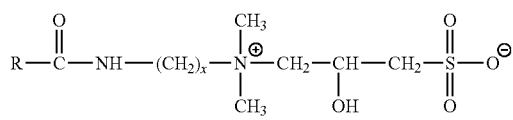

where RCO=$C_6$-$C_{24}$ acyl (saturated or unsaturated) or mixtures thereof. Examples include Cocamidopropyl Hydroxysultaine (RCO=coco acyl, x=3), Lauramidopropyl Hydroxysultaine (RCO=lauroyl, and x=3), Myristamidopropyl Hydroxysultaine (RCO=myristoyl, and x=3), and Oleamidopropyl Hydroxysultaine (RCO=oleoyl, and x=3).

Alkylamidoalkyl sultaines

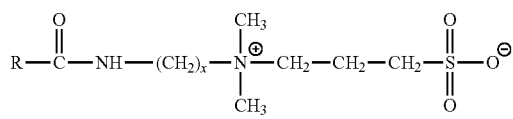

where RCO=$C_6$-$C_{24}$ acyl (saturated or unsaturated) or mixtures thereof. Examples include Cocamidopropyl Sultaine (RCO=coco acyl, x=3), Lauramidopropyl Sultaine (RCO=lauroyl, and x=3), Myristamidopropyl Sultaine (RCO=myristoyl, and x=3), Soyamidopropyl Betaine (RCO=soy acyl, x=3), and Oleamidopropyl Betaine (RCO=oleoyl, and x=3).

Alkyl phosphobetaines

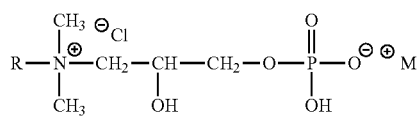

where R=$C_6$-$C_{24}$ alkyl (saturated or unsaturated) or mixtures thereof and $M^+$=monovalent cation, such as Sodium Coco PG-Dimonium Chloride Phosphate, where R=coco alkyl and $M^+$=$Na^+$.

Phospholipids

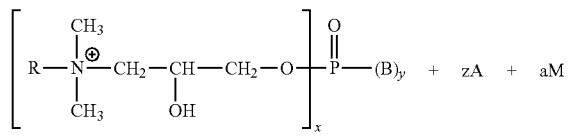

where R=$C_6$-$C_{24}$ alkyl (saturated or unsaturated) or mixtures thereof, x=1-3 or mixtures thereof, x+y=3, z=x, a=0 to 2, B=$O^-$ or OM, A=Anion, and M=Cation (refer to U.S. Pat. Nos. 5,215,976; 5,286,719; 5,648,348; and 5,650,402), such as Sodium Coco PG-Dimonium Chloride Phosphate, where R=coco alkyl, x=2, B=$O^-$, y=1, z=1, A=$Cl^-$, a=1, and M=$Na^+$.

Phospholipids

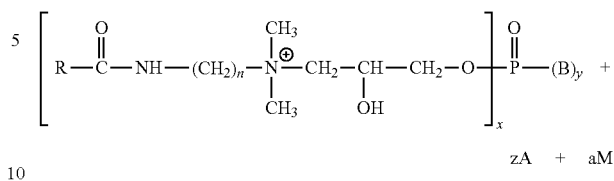

where RCO=$C_6$-$C_{24}$ acyl (saturated or unsaturated) or mixtures thereof, n=1-4, x=1-3 or mixtures thereof, x+y=3, z=x, a=0 to 2, B=$O^{31}$ or OM, A=anion, and M=cation (refer to U.S. Pat. Nos. 5,215,976; 5,286,719; 5,648,348; and 5,650, 402). Examples include Cocamidopropyl PG-Dimonium Chloride Phosphate (RCO=coco acyl, n=3, x=3, z=3, A=$Cl^-$, B and M are absent, y=0, and a=0) and Myristamidopropyl PG-Dimonium Chloride Phosphate (RCO=myristoyl, n=3, x=3, z=3, A=$Cl^-$, B and M are absent, y=0, and a=0).

Alkyl amphoacetates

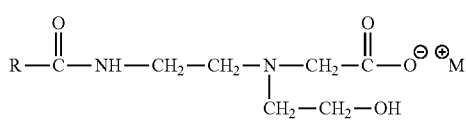

where RCO=$C_6$-$C_{24}$ acyl (saturated or unsaturated) or mixtures thereof and $M^+$=monovalent cation. Examples include Sodium Lauroamphoacetate (RCO=lauroyl and $M^+$=$Na^+$) and Sodium Cocoamphoacetate (RCO=coco acyl and $M^+$=$Na^+$).

Alkyl amphodiacetates

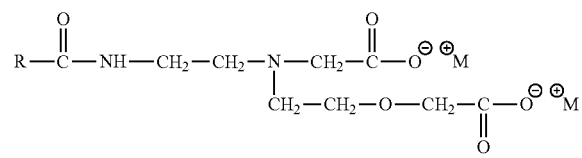

where RCO=$C_6$-$C_{24}$ acyl (saturated or unsaturated) or mixtures thereof and $M^+$=monovalent cation. Examples include Disodium Lauroamphodiacetate (RCO=lauroyl and M=$Na^+$) and Disodium Cocoamphodiacetate (RCO=coco acyl and M=$Na^+$).

Alkyl amphopropionates

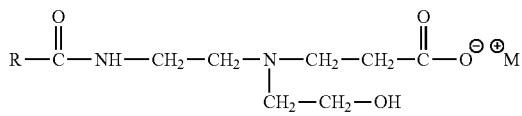

where RCO=$C_6$-$C_{24}$ acyl (saturated or unsaturated) or mixtures thereof and $M^+$=monovalent cation. Examples include Sodium Lauroamphopropionate (RCO=lauroyl and $M^+$=$Na^+$) and Sodium Cocoamphopropionate (RCO=coco acyl and $M^+$=$Na^+$).

Alkyl amphodipropionates

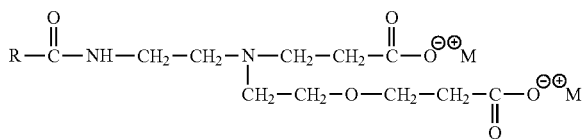

where RCO=$C_6$-$C_{24}$ acyl (saturated or unsaturated) or mixtures thereof and $M^+$=monovalent cation. Examples include Disodium Lauroamphodipropionate (RCO=lauroyl and $M^+$=$Na^+$) and Disodium Cocoamphodipropionate (RCO=coco acyl and $M^+$=$Na^+$).

Alkyl amphohydroxypropylsulfonates

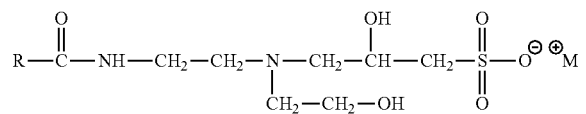

where RCO=$C_6$-$C_{24}$ acyl (saturated or unsaturated) or mixtures thereof and $M^+$=monovalent cation, such as Sodium Lauroamphohydroxypropylsulfonate (RCO=lauroyl and $M^+$=$Na^+$) and Sodium Cocoamphohydroxypropylsulfonate (RCO=coco acyl and $M^+$=$Na^+$).

Alkyl amphohydroxyalkylphosphates

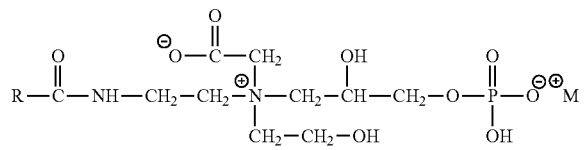

where RCO=$C_6$-$C_{24}$ acyl (saturated or unsaturated) or mixtures thereof and $M^+$=monovalent cation, such as Sodium Lauroampho PG-Acetate Phosphate (RCO=lauroyl and $M^+$=$Na^+$).

Alkyl amine oxides

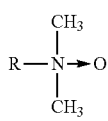

where R=$C_6$-$C_{24}$ alkyl (saturated or unsaturated) or mixtures thereof. Examples include Cocamine Oxide (R=coco alkyl) and Lauramine Oxide (RCO=lauryl).

Alkylamidoalkyl amine oxides

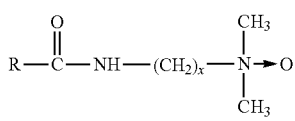

where RCO=$C_6$-$C_{24}$ acyl (saturated or unsaturated) or mixtures thereof and x=1-4. Examples include Cocamidopropylamine Oxide (RCO=coco acyl, x=3) and Lauramidopropylamine Oxide (RCO=lauroyl, x=3), and combinations of two or more thereof, and the like.

Any of a variety of ethoxylated nonionic surfactants are suitable for use in the present invention. Examples of suitable nonionic surfactants include, but are not limited to: fatty alcohol, fatty acid, or fatty amide ethoxylates; monoglyceride ethoxylates; sorbitan ester ethoxylates; mixtures thereof; and the like. Certain preferred ethoxylated nonionic surfactants include polyethyleneoxy derivatives of polyol esters, wherein the polyethyleneoxy derivative of polyol ester (1) is derived from (a) a fatty acid containing from about 8 to about 22, and preferably from about 10 to about 14 carbon atoms, and (b) a polyol selected from sorbitol, sorbitan, glucose, α-methyl glucoside, polyglucose having an average of about 1 to about 3 glucose residues per molecule, glycerol, pentaerythritol and mixtures thereof, (2) contains an average of from about 10 to about 120, and preferably about 20 to about 80 ethyleneoxy units; and (3) has an average of about 1 to about 3 fatty acid residues per mole of polyethyleneoxy derivative of polyol ester. Examples of such preferred polyethyleneoxy derivatives of polyol esters include, but are not limited to PEG-80 Sorbitan Laurate and Polysorbate 20.

While the compositions may comprise ethoxylated materials as described above in accord with certain embodiments, according to certain other embodiments, the compositions of the present invention are substantially free of ethoxylated materials. As used herein, the term "substantially free of ethoxylated materials" means a composition that comprises less than 1% by weight of total ethoxylated materials. In preferred embodiments, compositions that are substantially free of ethoxylated materials comprise less than 0.5%, more preferably less than 0.1%, and even more preferable are free of, ethoxylated materials.

As used herein, the term "ethoxylated material" means a material comprising one or more moieties derived from or prepared by the ring-opening oligomerization or polymerization of ethylene oxide and comprising one or more oxyethylene (—$CH_2CH_2O$—) moieties. Examples of ethoxylated materials include, but are not limited to, ethoxylated surfactants, emulsifiers, solubilizers, rheology modifiers, conditioning agents, preservatives, and the like, such as, for example anionic surfactants: polyoxyethylene alkyl ether sulfates (a.k.a. alkyl ether sulfates), polyoxyethylene alkyl ether carboxylates (a.k.a. alkyl ether carboxylates), polyoxyethylene alkyl ether sulfosuccinate esters; nonionic surfactants, emulsifiers, and solubilizers: polyoxyethylene alkyl ethers and esters, polysorbates, ethoxylated sorbitan fatty acid esters, ethoxylated glyceryl fatty acid esters, poloxamers; rheology modifiers: polyoxyethylene esters (e.g. PEG-150 Distearate), ethyoxylated alkyl glucoside esters (e.g. PEG-120 Methyl Glucose Trioleate), acrylic copolymers with ethoxylated associative macromonomers (e.g. Acrylates/Steareth-20 Methacrylate Copolymer), ethoxylated cellulose ethers (e.g. Hydroxyethylcellulose); conditioning agents: ethoxylated polyquaterniums (e.g. Polyquaternium-10); and the like.

Any of a variety of non-ethoxylated nonionic surfactants are also suitable for use in the present invention. Examples of suitable non-ethoxylated nonionic surfactants include alkyl polyglucosides, alkyl polypentosides, polyglyceryl esters, polyglyceryl ethers, polyglyceryl sorbitan fatty acid esters, sucrose esters, and sorbitan esters, and combinations of two or more thereof and the like. Certain preferred non-ethoxylated nonionic surfactants include $C_8$-$C_{18}$ polyglyceryl monoesters (e.g. polyglyceryl-4 caprylate/caprate, polyglyceryl-10 caprylate/caprate, polyglyceryl-4 caprate, polyglyceryl-10 caprate, polyglyceryl-4 laurate, polyglyceryl-5 laurate, polyglyceryl-6 laurate, polyglyceryl-10 laurate, polyglyceryl-10 cocoate, polyglyceryl-10 myristate, polyglyceryl-10 oleate, polyglyceryl-10 stearate, and combinations of two or more thereof) and $c_8$-$c_{18}$ polyglyceryl monoethers (e.g. polyglyceryl-4 lauryl ether, polyglyceryl-10 lauryl ether.

Another class of suitable nonionic surfactants includes long chain alkyl glucosides or polyglucosides, which are the condensation products of (a) a long chain alcohol containing from about 6 to about 22, and preferably from about 8 to about 14 carbon atoms, with (b) glucose or a glucose-containing polymer. Preferred alkyl glucosides comprise from about 1 to about 6 glucose residues per molecule of alkyl glucoside. A preferred glucoside is Decyl Glucoside, which is the condensation product of decyl alcohol with a glucose polymer and is available commercially from Cognis Corporation of Ambler, Pa. under the trade name, "Plantaren 2000N UP." Other examples include Coco-Glucoside and Lauryl Glucoside.

The compositions of the present invention may comprise any of a variety of additional other ingredients used conventionally in healthcare/personal care compositions ("personal care components"). These other ingredients nonexclusively include one or more, pearlescent or opacifying agents, thickening agents, emollients, secondary conditioners, humectants, chelating agents, actives, exfoliants, and additives which enhance the appearance, feel and fragrance of the compositions, such as colorants, fragrances, preservatives, pH adjusting agents, and the like.

Compositions useful in the present invention may also include any of a variety of conventional thickening agents. Examples of such thickening agents include: electrolytes (e.g. Sodium Chloride, Ammonium Chloride, Magnesium Chloride); naturally-derived polysaccharides (e.g. Xanthan Gum, Dehydroxanthan Gum, *Cyamopsis Tetragonoloba* (Guar) Gum, Cassia Gum, *Chondrus Crispus* (Carrageenan) Gum, Alginic Acid and alginate gums (Algin, Calcium Alginate, etc.), Gellan Gum, Pectin, Microcrystalline Cellulose); derivatives of natural polysaccharides (e.g. Hydroxyethylcellulose, Ethyl Hydroxyethylcellulose, Cetyl Hydroxyethylcellulose, Methylcellulose, Hydroxypropylcellulose, Sodium Carboxymethylcellulose, Hydroxypropyl Methylcellulose, Hydroxypropyl Guar, Carboxymethyl Hydroxypropyl Guar, C18-22 Hydroxylalkyl Hydroxypropyl Guar); alkali-swellable emulsion (ASE) polymers (e.g. Acrylates Copolymer, available under the trade name Carbopol® AQUA SF-1 from Noveon Consumer Specialties, Brecksville, Ohio, and Acrylates Copolymer available under the trade name Aculyn™ 33 from Dow Personal Care, Spring House, Pa.); hydrophobically-modified alkali-swellable emulsion (HASE) polymers (e.g. Acrylates/Steareth-20 Methacrylate Copolymer, Acrylates/Steareth-20 Methacrylate Crosspolymer, and Acrylates/Ceteth-20 Itaconate Copolymer); hydrophobically-modified acid-swellable emulsion polymers (e.g. Acrylates/Aminoacrylates/C10-30 Alkyl PEG-20 Itaconate Copolymer and Polyacrylate-1 Crosspolymer); hydrophobically-modified acrylate crosspolymers, such as Acrylates C10-30 Alkyl Acrylates Crosspolymer, available under the trade name Carbopol® 1382 from Lubrizol Corp., Brecksville, Ohio; and hydrophobic non-ethoxylated micellar thickeners (e.g. Glyceryl Oleate, Cocamide MIPA, Lauryl Lactyl Lactate, or Sorbitan Sesquicaprylate).

Any of a variety of skin and/or hair conditioning agents in addition to the cationic polyglyceryl compositions are suitable for use in this invention. Examples include: cationic surfactants (e.g. Cetrimonium Chloride, Stearamidopropyl Dimethylamine, Distearyldimonium Chloride, Lauryl Methyl Gluceth-10 Hydroxypropyldimonium Chloride); cationic polymers (e.g. cationically-modified polysaccharides, including Polyquaternium-10, Polyquaternium-24, Polyquaternium-67, Starch Hydroxypropyltrimonium Chloride, Guar Hydroxypropyltrimonium Chloride, and Hydroxypropyl Guar Hydroxypropyltrimonium Chloride, and cationic polymers derived from the (co)polymerization of ethylenically-unsaturated cationic monomers with optional hydrophilic monomers, including Polyquaternium-5, Polyquaternium-6, Polyquaternium-7, Polyquaternium-11, Polyquaternium-14, Polyquaternium-15, Polyquaternium-28, Polyquaternium-39, Polyquaternium-44; Polyquaternium-76); silicones and silicone derivatives (e.g. Dimethicone and derivatives thereof, such as alkyl-, polyalkyloxy-, cationically-, anionically-modified dimethicone (co)polymers); and emollients (e.g. Caprylic/Capric Triglycerides, Mineral Oil, Petrolatum, Di-PPG-2 Myreth-10 Adipate).

Any of a variety of humectants in addition to the cationic polyglyceryl compositions, which are capable of providing moisturization and conditioning properties to the personal cleansing composition, are suitable for use in the present invention. Examples of suitable humectants nonexclusively include polyols, such as Glycerin, Propylene Glycol, 1,3-Propanediol, Butylene Glycol, Hexylene Glycol, polyglycerins (e.g. Polyglycerin-3, Polyglyceryn-6, Polyglycerin-10), polyethylene glycols (PEGs), and polyoxyethylene ethers of α-methyl glucose, such as Methyl Gluceth-10 and Methyl Gluceth-20.

Examples of suitable chelating agents include those which are capable of protecting and preserving the compositions of this invention. Preferably, the chelating agent is ethylenediamine tetraacetic acid ("EDTA"), and more preferably is Tetrasodium EDTA or Tetrasodium Glutamate Diacetate.

Suitable preservatives include, for example, organic acids, parabens (e.g. Methylparaben, Ethylparaben, Propylparaben, Butylparaben, Isobutylparaben), quaternary ammonium species (e.g. Quaternium-15), phenoxyethanol, DMDM hydantoin, Diazolidinyl Urea, Imidazolidinyl Urea, Iodopropynyl Butylcarbamate, Methylisothazolinone, Methylchloroisothizaolinone, Benzyl Alcohol, Caprylyl Glycol, Decylene Glycol, Ethylhexylglycerin, and Gluconolactone. Preferred are organic acid preservatives that comprise at least one carboxylic acid moiety and are capable of preserving a composition of the present invention against microbial contamination Examples of suitable organic acids include Benzoic Acid and alkali metal and ammonium salts thereof (e.g. Sodium Benzoate and the like), Sorbic Acid and alkali metal and ammonium salts thereof (e.g. Potassium Sorbate and the like), p-Anisic Acid and alkali metal and ammonium salts thereof, Salicylic Acid and alkali metal and ammonium salts thereof, and the like. In certain preferred embodiments, the organic acid preservative comprises Benzoic Acid/Sodium Benzoate, Sorbic Acid/Potassium Sorbate, or combinations thereof.

The pH of the composition may be adjusted to the appropriate value using any number of cosmetically acceptable pH adjusters, including: alkali metal and ammonium hydroxides (e.g. Sodium Hydroxide, Potassium Hydroxide), alkali metal and ammonium carbonates (e.g. Potassium Carbonate), organic acids (e.g. Citric Acid, Acetic Acid, Glycolic Acid, Lactic Acid, Malic acid, Tartaric Acid), and inorganic acids (e.g. Hydrochloric Acid, Phosphoric Acid), and the like. In certain preferred embodiments, the pH is adjusted to be from 3 to 10, in certain more preferred embodiments, from 5 to 9, including from 6 to 8. In certain preferred embodiments, the electrolyte concentration of the composition is less than 10% by weight, more preferably less than 5%, more preferably less than 2%.

The cationic polyglyceryl compositions, optional surfactants and optional other components of the composition may be combined according to the present invention via any conventional methods of combining two or more fluids or solids. For example, one or more compositions comprising, consisting essentially of, or consisting of at least one cationic polyglyceryl compositions and one or more compositions comprising, consisting essentially of, or consisting of water, surfactants or suitable ingredients may be combined by pouring, mixing, adding dropwise, pipetting, pumping, and the like, one of the compositions comprising the cationic polyglyceryl compositions into or with the other in any order using any conventional equipment such as a mechanically stirred propeller, paddle, and the like.

The methods of the present invention may further comprise any of a variety of steps for mixing or introducing one or more of the optional components described hereinabove with or into a composition comprising a cationic polyglyceryl compositions either before, after, or simultaneously with the combining step described above. While in certain embodiments, the order of mixing is not critical, it is preferable, in other embodiments, to pre-blend certain components, such as the fragrance and the nonionic surfactant before adding such components into a composition comprising the cationic polyglyceryl compositions.

The compositions useful in the present invention involve formulations suitable for administering to the target tissues, such as mammalian skin such as human skin. In one embodiment, the composition comprises a cationic polyglyceryl compositions and a base, preferably a cosmetically-acceptable base. As used herein, the term "cosmetically-acceptable base" means a base that is suitable for use in contact with the skin without undue toxicity, incompatibility, instability, irritation, allergic response, and the like. This term is not intended to limit the base for use solely as a cosmetic (e.g., the ingredient/product can be used as a pharmaceutical).

The compositions may be made into a wide variety of product types that include but are not limited to cleansing liquid washes, gels, sticks, sprays, solid bars, shampoos, pastes, foams, powders, mousses, shaving creams, wipes, patches, wound dressing and adhesive bandages, hydrogels, films and make-up such as foundations, mascaras, and lipsticks. These product types may comprise several types of cosmetically-acceptable carriers including, but not limited to solutions, emulsions (including microemulsions and nanoemulsions), suspensions, gels, and solids. The following are non-limitative examples of such carriers. Other carriers can be formulated by those of ordinary skill in the art.

The compositions of the present invention may comprise water. In certain preferred embodiments, the composition comprises greater than 60%, more preferably from 70-95% water.

The compositions useful in the present invention can be formulated as solutions. Solutions typically include an aqueous or organic solvent (e.g., from about 50% to about 99.99% or from about 90% to about 99% of a cosmetically acceptable aqueous or organic solvent). Examples of suitable organic solvents include: polyglycerols, propylene glycol, polyethylene glycol (200, 600), polypropylene glycol (425, 2025), glycerol, 1,2,4-butanetriol, sorbitol esters, 1,2,6-hexanetriol, ethanol, and mixtures thereof. In certain preferred embodiments, the compositions of the present invention are aqueous solutions comprising from about 50% to about 99% by weight of water.

According to certain embodiments, compositions useful in the subject invention may be formulated as a solution comprising an emollient. Such compositions preferably contain from about 2% to about 50% of an emollient(s). As used herein, "emollients" refer to materials used for the prevention or relief of dryness, as well as for the protection of the skin. A wide variety of suitable emollients are known and may be used herein. A lotion can be made from such a solution. Lotions typically comprise from about 1% to about 20% (e.g., from about 5% to about 10%) of an emollient(s) and from about 50% to about 90% (e.g., from about 60% to about 80%) of water.

The compositions of this invention can also be formulated as a gel (e.g., an aqueous, alcohol, alcohol/water, or oil gel using a suitable gelling agent(s)). Suitable gelling agents for aqueous and/or alcoholic gels include, but are not limited to, natural gums, acrylic acid and acrylate polymers and copolymers, and cellulose derivatives (e.g., hydroxymethyl cellulose and hydroxypropyl cellulose). Suitable gelling agents for oils (such as mineral oil) include, but are not limited to, hydrogenated butylene/ethylene/styrene copolymer and hydrogenated ethylene/propylene/styrene copolymer. Such gels typically comprises between about 0.1% and 5%, by weight, of such gelling agents.

The present compositions may be of varying phase compositions, but are preferably aqueous solutions or otherwise include an exterior aqueous phase (e.g., aqueous phase is the most exterior phase of the composition). As such, compositions of the present invention may be formulated to be oil-in-water emulsions that are shelf-stable in that the emulsion does not lose phase stability or "break" when kept at standard conditions (22 degrees Celsius, 50% relative humidity) for a week or more after it is made.

In certain embodiments, the compositions produced via the present invention are preferably used as or in healthcare products for treating or cleansing at least a portion of a mammalian body, for example, the human body. Examples of certain preferred personal care products include various products suitable for application to the skin, hair, oral and/or perineal region of the body, such as shampoos, hand, face, and/or body washes, bath additives, gels, lotions, creams, and the like. As discussed above, applicants have discovered unexpectedly that the instant methods provide personal care products having reduced irritation to the skin and/or eyes and, in certain embodiments one or more of desirable properties such as flash foaming characteristics, rheology, and functionality, even at high surfactant concentrations. Such products may further include a substrate onto which a composition is applied for use on the body. Examples of suitable substrates include a wipe, pouf, sponge, and the like as well as absorbent articles, such as a bandage, sanitary napkin, tampon, and the like.

The present invention provides methods of treating and/or cleansing the human body comprising contacting at least a portion of the body with a composition of the present invention. Certain preferred methods comprising contacting mammalian skin, hair and/or vaginal region with a composition of the present invention to cleanse such region and/or treat such region for any of a variety of conditions including, but not limited to, acne, wrinkles, dermatitis, dryness, muscle pain, itch, and the like. In certain preferred embodiments, the contacting step comprises applying a composition of the present invention to human skin, hair or vaginal region. The cleansing methods of the present invention may further comprise any of a variety of additional, optional steps associated conventionally with cleansing hair and skin including, for example, lathering, rinsing steps, and the like.

EXAMPLES

The following test methods and procedures were used:

Degree of Reaction Conversion of Polyglyceryl or
Polyglyceryl Ester with
3-chloro-2-hydroxypropyldimethylalkylammonium
chloride (CHADAC)

In the following description, chlorine refers to all Cl species (as both free ions and covalently bound). As seen in the scheme below, the CHADAC reagent contains covalently bound chlorine. Covalently bound chlorine refers to Cl species covalently bonded to the 2-hydroxypropyl species of CHADAC reagents and is referred to as $Cl_b$. The CHADAC reagent also contains a chloride counterion, referred to as $Cl_c$. During the reaction, the CHADAC reagent is consumed and yields an additional mole of $Cl_c$. Reaction conversion was determined by measuring the change in $Cl_c$ concentration.

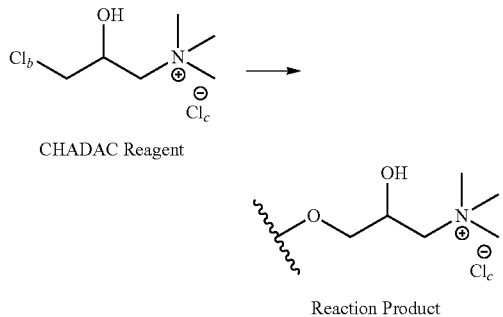

CHADAC Reagent

Reaction Product

In the following description $Cl_a$ refers to the sum of bound chlorine ($Cl_b$) and chloride counterion ($Cl_c$) species. Below, the subscripts t=0 and t=f (with respect to $Cl_a$, $Cl_b$ and $Cl_c$) refer to the initial starting time and final time after the reaction.

The percent conversion of the reaction was determined by the following equation:

$$\% \text{ Conversion} = \left(1 - \frac{\text{mol } Cl_{b,t=f}}{\text{mol } Cl_{b,t=0}}\right) \times 100$$

Where the mol $Cl_{b,f}$ and mol $Cl_{b,f}$ may be determined by $$\text{mol } Cl_{b,t=0} = \frac{g \ CHADAC \times wt \ \% \ Cl_{b,t=0}}{MW_{Cl}}$$

where the g CHADAC refers to the mass of CHADAC reagent utilized in the reaction, g Reaction refers to the total mass of the reaction, and $MW_{Cl}$ refers to the molecular weight of chlorine. The wt % $Cl_{b,t=0}$ and wt % $Cl_{b,t=f}$ are determined by the equations wt % $Cl_{b,t=0}$=wt % $Cl_{a,t=0}$−wt % $Cl_{c,t=0}$ wt % $Cl_{b,t=f}$=wt % $Cl_{a,t=f}$−wt % $Cl_{c,t=f}$ where the wt % $Cl_{a,t=0}$, wt % $Cl_{c,t=0}$, wt % $Cl_{a,t=f}$, wt % $Cl_{c,t=f}$ are measured directly by titration.

Titration experiments were conducted as follows: on a suitable balance, the reaction product was accurately weighed, transferred into a 500 mL Erlenmeyer flask, and subsequently dispersed or dissolved in 10 mL of 1.5% hydrogen peroxide solution. Approximately 40 mL of isopropanol was added and mixed followed by the addition of approximately 0.5 mL of 0.13% diphenylcarbazone in ethanol solution. The resulting solution was then titrated with previously standardized 0.003 M mercuric acetate volumetric solution loaded in a microburet to a pink endpoint. If necessary the endpoint of a blank solution was determined. The wt % $Cl_c$ is determined by $$\% \ Cl_c = \frac{(V_{spl} - B) \times K_{Cl} \times 100}{Wt_{sample}}$$

where $Wt_{sample}$ is the weight of the sample in μg, $V_{Spl}$ is the sample titration volume in mL, B is the blank titration volume in mL, and $K_{Cl}$ is the equivalency factor of mercuric acetate volumetric solution in μg/mL.

Foam Test:

The following Foam Test was performed on various test compositions to determine the foam volume upon agitation according to the present invention. First, 1.0 g of test material (e.g., polyglyceryl composition), on an active basis, is added to a beaker. Then 500 g of a 0.72 g/L calcium chloride solution was added to the beaker, and deionized water was added to bring the final mass to 1000 g. As such a test composition was formed with 0.1% active polyglyceryl composition (or comparative composition) in simulated hard water. To determine the foam volume, the test composition (1000 mL) was added to a sample tank of a SITA R-2000 foam tester (commercially available from Future Digital Scientific, Co.; Bethpage, N.Y.). The test parameters were set to repeat three runs (series count=3) of 250 ml sample size (fill volume=250 ml) with thirteen stir cycles (stir count=13) for a 15 second stir time per cycle (stir time=15 seconds) with the rotor spinning at 1200 RPM (revolution=1200) at a temperature setting of 30° C.±2° C. Foam volume data was collected at the end of each stir cycle and the average and standard deviations for the three runs was determined. The foam volume after the thirteenth stir cycle is recorded as the maximum foam volume, Foam $Volume_{max}$. The volume of foam 18 minutes after the Foam $Volume_{max}$ has been achieved is recorded as Foam $Volume_{t=18 \ min}$. The % foam volume retention is then determined by the following equation $$\% \text{ Foam Volume Retention} = 100 \times \frac{\text{Foam } Volume_{t=18 \ min}}{\text{Foam } Volume_{max}}$$

Zero Shear Viscosity Test:

The following Zero Shear Viscosity Test was performed on various personal care compositions to determine the viscosity according to the present invention. Viscosities of test formulations were conducted at 25° C. using a controlled-stress rheometer (AR-2000, TA Instruments Ltd., New Castle, Del., USA). Steady-state shear stress sweeps were performed at 25.0±0.1° C. using a double-wall Couette geometry. Data acquisition and analysis were performed with the Rheology Advantage software v4.1.10 (TA Instruments Ltd., New Castle, Del., USA). Zero-shear apparent viscosities for samples that demonstrated Newtonian behavior are reported as the average of viscosity values obtained over a range of shear stresses (i.e. 0.1-100 dynes/cm²). For pseudoplastic (shear-thinning) fluids, zero-shear apparent viscosities ($\eta_0$) were calculated via the fitting of shear stress sweep data to an Ellis or Carreau viscosity model.

The Relative Viscosity, $\eta_{relative}$ was determined by the following equation, $$\eta_{relative} = \frac{\eta_{0 \ Example}}{\eta_{0 \ Base}}$$

where $\eta_{example}$ is the zero shear viscosity of a formula with an inventive or comparative material and $\eta_{0 \ base}$ is the zero shear viscosity of the "base formula," i.e., without the particular test composition. Thus $\eta_{relative}$ is a measure of how well a particular test composition (e.g., cationic polyglyceryl composition) increases viscosity of the base formula. The error associated with zero shear viscosity measurements in accord with this procedure is less than 5%.

Conditioning Test:

The following Conditioning Test was performed by applying a personal care test composition to hair and evaluating for wet feel based on combing. Instron mechanical combing tests developed at Textile Research Institute (TRI, Princeton, N.J.) were utilized to evaluate these properties. The tested formulas were applied to 6 inch virgin medium brown tresses which had been bleached for 40 minutes at 40° C. using 6% $H_2O_2$. The procedure was as follows: dry hair tresses were treated under flowing water for 30 seconds. Excess water was removed from each tress with a squeegee motion using the fingers. The tress was wet again for an additional 30 seconds, squeegeed once, then 0.3 mL of personal care test composition was applied and lathered into the tress for 30 seconds. After lathering, the tress was combed with a coarse-toothed comb to remove tangles and then with a second comb similar to the comb mounted on the Instron tensile tester. Standard wet tress combing was run on the Instron tensile tester, Instron 1122 with 5500R electronics and software. The tress was then smoothed between the fingers and mounted in the grips of the Instron. The combing was repeated 5 times, smoothing the tress after each pass. After five passes the tress was removed from the grips and rinsed under flowing water to yield a cumulative rinse time of 15, 30, and 60 seconds. The average load after a 60 second cumulative rinse time is reported as the "Average Comb Force" with units of grams force (gf). The average load was determined by measuring the force exerted through the first through fourth inch of the tress during the second and third comb stroke. If the maximum load (268 gf) of the instrument was reached before the comb passed through the fourth inch of the tress, the instrument did not record an average load and a value of 268 gf was assigned. The number of tangle events was determined from the average number of strokes that reached a max force of 268 gf during the 0 to 6th inch of combing the tress. The "% of tangled strokes" were taken as the number of tangle events which occurred during strokes 1-4 taken from 0, 15, 30, and 60 cumulative rinse times divided by the number of total strokes. The fifth combing step was not used in data analysis due to the significant amount of work previously conducted on the hair with comb steps 1-4.

Water Sorption Test:

The following Water Sorption Test was performed using the technique of dynamic vapor sorption (DVS). For each test composition, samples were placed in sample pans and inserted into a DVS Intrinsic Instrument (available from Surface Measurement Systems of Allentown, Pa.) and allowed to equilibrate at 25° C., 20% relative humidity (RH) until the target dm/dt (change in mass/change in time) equilibration parameter of 0.001% was reached. The humidity was increased in 10% RH increments up to 90% RH, and then increased to 98% RH as the maximum humidity step. Following the RH ramp, the humidity was decreased from 98% RH to 90% RH, followed by a decrease in RH by 10% increments until 20% RH was reached. RH steps were programmed to occur once equilibration was obtained (0.001% dm/dt) or after 240 min if equilibration was not obtained within the timeframe. Measurements were taken every five seconds during the entire duration of the experiment.

The % change in mass at 50% RH was measured as both a sorption and desorption process. During the sorption process, the % change in mass (% $\Delta Mass_{50\ RH\ sorp}$) is calculated using the following equation, $$\%\ \Delta Mass_{50\ RH\ sorp} = \frac{Wt_{20 \to 50\ RH} - Wt_{ref}}{Wt_{ref}} \times 100$$

where the $Wt_{20 \to 50RH}$, refers to the equilibrium (or pseudoequilibrium) weight of the sample at 50% RH as the chamber humidity was increased from 20 to 50% RH. $Wt_{ref}$ refers to the equilibrium weight of the sample at 20% RH after being placed in the chamber from atmospheric conditions. The average value of % $\Delta Mass_{50\ RH\ sorp}$ for three samples is reported.

Similarly, the % change in mass during the desorption process (% $\Delta Mass_{50\ RH\ desorp}$) was calculated using the following equation, $$\%\ \Delta Mass_{50\ RH\ desorp} = \frac{Wt_{98 \to 50\ RH} - Wt_{ref}}{Wt_{ref}} \times 100$$

where the $Wt_{98 \to 20RH}$, refers to the equilibrium (or pseudoequilibrium) weight of the sample at 50% RH as the chamber humidity was decreased from 98 to 50% RH. The $Wt_{ref}$ again refers to the equilibrium weight of the sample at 20% RH after being placed in the chamber from atmospheric conditions.

Those skilled in the art will recognize that sorption versus desorption values can be different based on the ability of the humectant to retain vs absorb water. Moisture retention of a humectant delivered from a water-based system may be more accurately gauged by the desorption equilibrium values, whereas moisture uptake is more accurately gauged by the sorption equilibrium values.

Anti-Frizz Test:

The following Anti-Frizz Test was performed. Mulatto Blended hair was acquired from International Hair Importers (IHI) and was supplied in rounded tresses of approximately 4 g weight (not including the epoxy plug) and straightened length of approximately 220 mm (not including the epoxy plug). Hair was pre-washed by IHI using a simple surfactant solution (no fragrance, color or other additives), and pre-combed at TRI to a common level of alignment prior to straightening. Prior to treatment with a personal care test composition, the 4 g mulatto hair tress was wet for 30 seconds under a shower head dispensing water at 40° C. and 1 gallon/minute. Subsequently, the personal care test composition was applied according to the following procedure: personal care test composition was added to the tress at 10% dosage based on weight of tress, massaged into the tress for 30 seconds, and rinsed for 30 seconds using 40° C. water at a flow rate of 1 gallon/minute. After treatment, the sample was blow dried and straightened with a brush. After each tress was thus set, it was hung in a controlled humidity chamber at 25% RH. Once all tresses were straightened, there was the need to quickly re-set the earlier prepared tresses which had begun to undergo some slight reversion even under low humidity conditions. Once all tresses were visually-judged to possess comparable straightness, the humidity was then raised to 50% and the experiment was begun. Following treatment each tress was placed on a pre-selected position on a board in the humidity chamber. The hair was illuminated by ambient light via a pair of vertically mounted fluorescent fixtures. Images of the hairmounting boards with 4 tresses were collected using a 12.9 Megapixel Fuji S-5pro digital camera. Images were acquired before, immediately after treatment, every 15 minutes for the first hour, 30 minutes for the subsequent 4 hours, and then every 60 minutes for the last 3 hours post treatment. Images were saved directly to the hard-drive of a computer controlling the camera.

The volume of individual tresses was determined using custom written software operating under Lab View™ v8.5. In the analysis, the tress was separated from the background by a thresholding technique. The resulting binary image was utilized in the calculation of frizz. The percent of frizz for each tress was calculated as a percentage of reversion as a function of time relative to the initial and final area of the tresses, $$\% \, Frizz = 100 \times \frac{A_t - A_0}{A}$$

where $A_t$ is equal to the area of tress at a specific time, t; $A_0$ is equal to the initial area of the straightened tress; and A is equal to the area of a non-straightened tress.

Example I

Preparation of Inventive Cationic Polyglyceryl Compositions and Compartive Examples The following abbreviations are used herein: PG-10=polyglyceryl-10, PG-10-1-O=polyglyceryl-10 monooleate, PG-10-1-L=polyglyceryl-10 monolaurate, PG-10-1-LE=polyglyceryl-10 lauryl ether, Quab® 342 (3-chloro-2-hydroxypropyl-lauryl-dimethylammonium chloride)=LD, Quab® 360 (3-chloro-2-hydroxypropyl-co-coalkyl-dimethylammonium chloride)=CD, and Quab® 188 (3-chloro-2-hydroxypropyl-trimethylammonium chloride) =TM. Polyglyceryl materials were obtained from available as Natrulon® H-10, Polyaldo® 10-1-O KFG, and Polyaldo® 10-1-L from Lonza PLC. The polyglyceryl material Polyglycerin Ether ML10 was obtained from Daicel Chemical Industries, Ltd. All Quab® reagents were obtained from SKW QUAB Chemicals, Inc of Mobile, Ala.

Cationic polyglyceryl composition, Inventive Example, E1 was synthesized as follows: to a clean, appropriately sized flask equipped with an overhead stirrer, a heating mantle/thermocouple connected to a temperature controller and N₂ sparge tube, deoxygenated polyglycerin-10 (0.120 mol, 115.16 g, 79% Active) and Quab® 360 (0.156 moles, 140.23 g, 40% active) were added. The mixture was lightly sparged with nitrogen gas for 10 minutes. Subsequently, the material was heated to 35° C. at a rate of 5° C./min. Once at 35° C., NaOH pellets (0.174 mol, 6.96 g) were added over the course of several minutes while mixing. After the addition of the NaOH pellets, the mixture was heated to 80° C. at a rate of 5° C./min. The solution was stirred at 80° C. for 5 hr after which the solution was allowed to come to room temperature. The cooled material was discharged to an appropriate container. Note that as an optional post-reaction step, the pH of some products was adjusted to below 7 via addition of acetic acid prior to being discharged.

Additional cationic polyglyceryl compositions, Inventive Examples E2-E16, were synthesized by varying the type or proportions of starting materials: polyglycerol vs polyglyceryl ester, base catalyst, CHADAC reagent, and/or addition of water. The variation in starting materials used, reaction conditions, and products are summarized in Table 1 below. When additional water was utilized it was added before sparging the polyol and CHADAC reagents.

For E6 and E16, the CHADAC reagents were added sequentially, with TM being added to the initial reaction mixture and CD being added after heating at 80° C. for 2.5 hrs. Reaction conditions and conversion data for E1-E16 are also shown in Table 1.

Comparative Examples, C1 and C2 compositions were synthesized in a similar manner as E1-E16. An example of the synthesis of C1 is as follows: to a clean, appropriately sized flask equipped with an overhead stirrer, a heating mantle/thermocouple connected to a temperature controller and N₂ sparge tube, deoxygenated polyglycerol (0.160 mol, 153.9 g, 79% active) and Quab® 188 (0.208 moles, 56.6 g, 69% active) were added. The mixture was lightly sparged with nitrogen gas for 10 minutes. Subsequently, the material was heated to 35° C. at a rate of 5° C./min. Once at 35° C., NaOH pellets (0.234 mol, 9.35 g) were added over the course of several minutes while mixing. After the addition of the NaOH pellets, the mixture was heated to 80° C. at a rate of 5° C./min. The solution was stirred at 80° C. for 5 hr after which the solution was allowed to come to room temperature. As an optional step, the pH of some products was adjusted to below 7 with the use of acetic acid. After neutralization of the reaction, the material was cooled and discharged to an appropriate container. Reaction conditions and conversion data for C1 and C2 are also shown in Table 1.

TABLE 1

Reaction conditions and conversion data for the synthesis of cationic polyglyceryl compositions and comparative examples.

| | Polyol | | CHADAC Reagent | | Mass | Moles | Time at 80° C. | % |
|---|---|---|---|---|---|---|---|---|
| Ex # | Type | Moles | Type | Moles | Water (g) | NaOH | (hr) | Conversion |
| E1 | PG-10 | 0.120 | CD | 0.156 | 0 | 0.174 | 5.00 | 102 |
| E2 | PG-10 | 0.120 | CD | 0.234 | 0 | 0.268 | 5.25 | 74 |
| E3 | PG-10 | 0.120 | LD | 0.156 | 0 | 0.182 | 8.00 | 105 |
| E4 | PG-10 | 0.470 | LD | 0.611 | 0 | 0.689 | 5.00 | 99 |
| E5 | PG-10 | 0.121 | TM + LD[1] | TM—0.28, LD—0.16 | 0 | 0.460 | 4.75 | 97 |
| E6 | PG-10 | 0.120 | TM + LD[2] | TM—0.27, LD—0.15 | 0 | 0.462 | 4.50 | 99 |
| E7 | PG-10-1-L | 0.124 | CD | 0.156 | 0 | 0.174 | 5.00 | 96 |
| E8 | PG-10-1-L | 0.124 | LD | 0.156 | 11.44 | 0.176 | 5.50 | 95 |
| E9 | PG-10-1-L | 0.124 | TM | 0.156 | 23.78 | 0.595 | 4.50 | 100 |

TABLE 1-continued

Reaction conditions and conversion data for the synthesis of cationic polyglyceryl compositions and comparative examples.

| Ex # | Polyol Type | Polyol Moles | CHADAC Reagent Type | CHADAC Reagent Moles | Mass Water (g) | Moles NaOH | Time at 80° C. (hr) | % Conversion |
|---|---|---|---|---|---|---|---|---|
| E10 | PG-10-1-L | 0.124 | TM | 0.446 | 0 | 0.463 | 4.50 | 92 |
| E11 | PG-10-1-L | 0.206 | TM | 0.467 | 24.52 | 0.488 | 6.00 | 89 |
| E12 | PG-10-1-LE | 0.120 | LD | 0.156 | 0 | 0.175 | 6.00 | 98 |
| E13 | PG-10-1-O | 0.120 | CD | 0.156 | 25.86 | 0.176 | 5.00 | 93 |
| E14 | PG-10-1-O | 0.120 | LD | 0.156 | 24.84 | 0.175 | 5.50 | 99 |
| E15 | PG-10-1-O | 0.200 | TM | 0.277 | 292.49 | 0.288 | 5.00 | 99 |
| E16 | PG-10-1-O | 0.120 | TM + LD[1] | TM—0.27, LD—0.16 | 24.51 | 0.467 | 4.75 | 97 |
| C1 | PG-10 | 0.160 | TM | 0.208 | 0 | 0.234 | 4.25 | 101 |
| C2 | PG-10 | 0.121 | TM | 0.401 | 0 | 0.445 | 4.25 | 102 |

[1]TM and LD added simultaneously.
[2]TM added first. LD added second.

Example II

Figure 3:
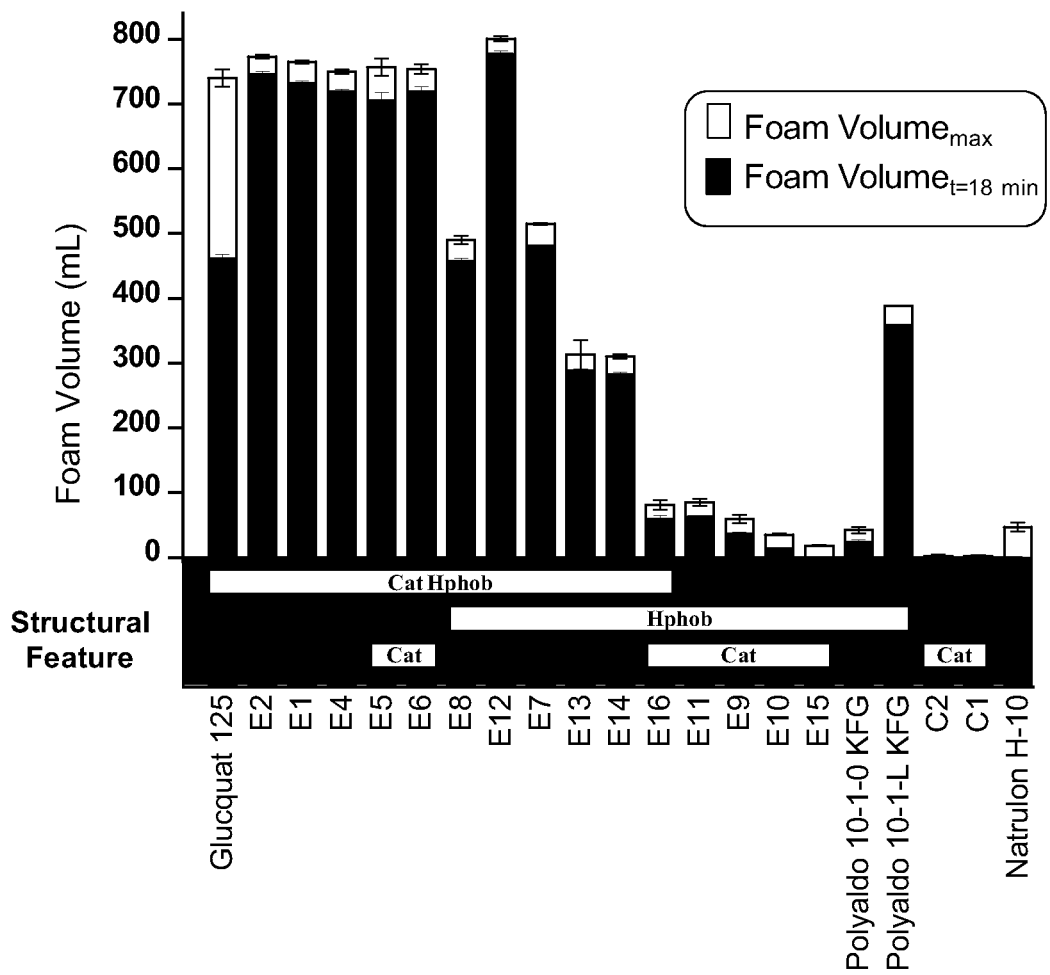
FIG. 3 is a graphical depiction of maximum foam volume and foam volume values of certain compositions of the present invention and comparable compositions.

Foam Properties of Inventive Cationic Polyglyceryl Compositions and Comparative Examples The compositions of Example I were tested according to the Foam Test, described above. The results, including maximum foam volume (Foam Volume$_{max}$), foam volume$_{t=18\,min}$, and % foam volume retention are given in Table 2 and FIG. 3. Ingredient names of inventive examples are based on the molar quantities of CHADAC reagents and PG/PGE reagent. With reference to FIG. 3, shown are maximum foam volume (mL) (white bar) and foam volume$_{t=18\,min}$ (black bar) of inventive and comparative examples in simulated hard water. The highlighted gray area indicates a portion of the graph which does not have meaningful y-axis values but has been included to allow space for the description of structural features. Structural features of inventive and comparative examples are noted as white horizontal bars transversing samples which contain the feature. Cat-Hphob=(L$_2$-R$_2$—N—[(R$_3$)(R$_4$)(Hphob$_2$)]). Cat=(L$_3$-R$_5$—N—[(R$_6$)(R$_7$)(R$_8$)]). Hphob=(L$_1$-R$_1$-Hphob$_1$).

TABLE 2

Foam properties of Inventive Cationic Polyglyceryl Compositions and Comparative Examples in Simulated Hard Water.

| Test Material/ Tradename | Ingredient Name | Foam Volume$_{max}$ (mL) | Foam Volume$_{t=18\,min}$ (mL) | % Foam Volume Retention |
|---|---|---|---|---|
| E1 | (CD)$_1$ PG-10 | 765 | 733 | 96 |
| E2 | (CD)$_2$ PG-10 | 773 | 747 | 97 |
| E4 | (LD)$_1$ PG-10 | 750 | 720 | 96 |
| E5 | (LD)$_1$(TM)$_2$ PG-10 | 757 | 706 | 93 |
| E6 | (LD)$_1$(TM)$_2$ PG-10 | 754 | 720 | 95 |
| E7 | (CD)$_1$ PG-10-1-L | 515 | 482 | 94 |
| E8 | (LD)$_1$ PG-10-1-L | 490 | 458 | 93 |
| E9 | (TM)$_1$ PG-10-1-L | 59 | 37 | 63 |
| E10 | (TM)$_3$ PG-10-1-L | 35 | 14 | 40 |
| E11 | (TM)$_2$ PG-10-1-L | 85 | 63 | 74 |
| E12 | (LD)$_1$ PG-10-1-LE | 801 | 778 | 97 |
| E13 | (CD)$_1$ PG-10-1-O | 313 | 289 | 92 |
| E14 | (LD)$_1$ PG-10-1-O | 310 | 283 | 91 |
| E15 | (TM)$_1$ PG-10-1-O | 18 | 0.7 | 4 |
| E16 | (LD)$_1$(TM)$_2$ PG-10-1-O | 81 | 60 | 74 |
| C1 | (TM)$_1$ PG-10 | 1.3 | 0 | 0 |
| C2 | (TM)$_3$ PG-10 | 1.7 | 0 | 0 |
| Natrulon H-10 | PG-10 | 47 | 0 | 0 |
| PG-10-1-L | PG-10-1-L | 388 | 359 | 93 |
| Polyaldo 10-1-O KFG | PG-10-1-O | 42 | 24 | 57 |
| Glucquat 125 | Lauryl methyl gluceth-10 hydroxypropyl dimonium Chloride | 740 | 462 | 62 |

Also tested were the following: Comparative Example Glucquat™ 125 (Lauryl Methyl Gluceth-10 Hydroxypropyldimonium Chloride, commercially available from Lubrizol Corp., Brecksville, Ohio), Comparative Example Polyaldo® 10-1-O (polyglyceryl-10 oleate available from Lonza Group PLC), and Comparative Example PG-10-1-L (polyglyceryl-10 laurate, also available from Lonza Group PLC).

Example III

Water Sorption Properties of Cationic Polyglyceryl Compositions and Comparative Examples Selected Inventive Examples described in Example I above, as well as Glucquat™ 125 were tested according to the Water Sorption Test, also described above. The results, including % ΔMass$_{50\,RH\,sorp}$, and % ΔMass$_{50\,RH\,desorp}$ are given in Table 3.

Table 3 shows water sorption data of comparative and inventive materials. The % mass change upon desorption (high to low RH) indicates the material is able to retain water once absorbed. Conversely, the % mass change upon sorption (low to high RH) indicates the ability of the material to absorb water.

TABLE 3

Water Sorption of Inventive Cationic Polyglyceryl
Compositions and Comparative Examples.

| Test Material/ Tradename/ | Ingredient Name | % $\Delta Mass_{50\,RH\,Sorp}$ | % $\Delta Mass_{50\,RH\,Desorp}$ |
|---|---|---|---|
| E4 | $(LD)_1$ PG-10 | 8.9 | 9.7 |
| E5 | $(LD)_1(TM)_2$ PG-10 | 13.1 | 22 |
| Glucquat 125 | Lauryl methyl gluceth-10 hydroxypropyl-dimonium | 8.1 | 8.2 |

Example IV

Preparation of Comparative and Inventive Personal Care Compositions

Personal care formulations were prepared using selected inventive examples of Example I. In addition, comparative personal care formulations were prepared using Glucquat™ 125, Polyaldo® 10-1-O, as well as no humectant. A premix comprised of quaternium-15 and a fraction of the required PEG-80 sorbitan laurate and deionized water was allowed to mix in a beaker until all the quaternium-15 had dissolved. To a separate beaker fitted with a mechanical stirrer and hotplate, water, PEG-150 distearate, and the remaining fraction of PEG-80 sorbitan laurate were added. This was mixed at low-medium speed and heat was slowly applied to the batch to increase the temperature to 80° C. The mixture was heated until all material was dissolved. Approximately one half of the required purified water was added to the beaker and allowed to mix until the temperature reached 60° C. Sodium trideceth sulfate, cocamidopropyl betaine, and tetrasodium edta were added to the mixture and allowed to cool to 40° C. The material was allowed to mix for 30 min. The premix was combined with the surfactant solution and allowed to mix for 20 min. When the temperature reached 25° C., the pH was adjusted to 6.5. A particular commercially available humectant or experimental material was added. The pH was checked to ensure it was within tolerance (6.5±0.3). Water was added in q.s. to 100%. The compositions of the various comparative compositions (and active weight percentages of ingredients) are shown in the Table 4a below while inventive personal care compositions are shown in Table 4b.

TABLE 4a

Comparative Personal Care Compositions.

| Test Material/ Tradename | Ingredient Name | C3 | C4 | C5 |
|---|---|---|---|---|
| Control (no Humectant) | Control (no Humectant) | — | — | — |
| Polyaldo 10-1-O KFG | PG-10-1-O | — | 1.00 | — |
| Glucquat 125 | Lauryl methyl gluceth-10 hydroxypropyldimonium chloride | — | — | 1.00 |
| Dowicil 200 | Quaternium-15 | 0.05 | 0.05 | 0.05 |
| Atlas G-4280 | PEG-80 Sorbitan Laurate | 3.60 | 3.60 | 3.60 |
| Ethox PEG-6000 DS Special | PEG-150 Distearate | 0.45 | 0.45 | 0.45 |
| Cedepal TD403 MFLD | Sodium Trideceth Sulfate | 2.70 | 2.70 | 2.70 |
| TEGO Betain L7V | Cocamidopropyl Betaine, | 3.75 | 3.75 | 3.75 |
| Versene 100 XL | Tetrasodium EDTA | 0.10 | 0.10 | 0.10 |
| Sodium Hydroxide solution (20%) | Sodium Hydroxide | q.s. | q.s. | q.s. |
| Citric Acid solution (20%) | Citric Acid | q.s. | q.s. | q.s. |
| Purified Water | Water | q.s. | q.s. | q.s. |

TABLE 4b

Inventive Personal Care Compositions.

| Test Material/ Tradename | Ingredient Name | E17 | E18 | E19 |
|---|---|---|---|---|
| E4 | $(LD)_1$ PG-10 | 1.00 | — | — |
| E5 | $(LD)_1(TM)_2$ PG-10 | — | 1.00 | — |
| E14 | $(LD)_1$ PG-10-1-O | — | — | 1.00 |
| Dowicil 200 | Quaternium-15 | 0.05 | 0.05 | 0.05 |
| Atlas G-4280 | PEG-80 Sorbitan Laurate | 3.60 | 3.60 | 3.60 |
| Ethox PEG-6000 DS Special | PEG-150 Distearate | 0.45 | 0.45 | 0.45 |
| Cedepal TD403 MFLD | Sodium Trideceth Sulfate | 2.70 | 2.70 | 2.70 |
| TEGO Betain L7V | Cocamidopropyl Betaine, | 3.75 | 3.75 | 3.75 |
| Versene 100 XL | Tetrasodium EDTA | 0.10 | 0.10 | 0.10 |
| Sodium Hydroxide solution (20%) | Sodium Hydroxide | q.s. | q.s. | q.s. |
| Citric Acid solution (20%) | Citric Acid | q.s. | q.s. | q.s. |
| Purified Water | Water | q.s. | q.s. | q.s. |

Example V

Conditioning Properties of Cationic Polyglyceryl Compositions and Comparative Examples The personal care compositions of Example IV were tested according to the Conditioning Test, described above, except that 8 tresses were used (n=8) per example. The results, including are given in Table 5. Inventive examples (E17-E19) have lower percentage of tangled strokes and lower average comb force (indicating better conditioning) as compared to Comparative Example, C3 (no humectant).

TABLE 5

Conditioning Properties of Hair Treated with
Comparative Examples and Inventive Examples.

| Example # | Avg Comb Force after 60 sec Rinse (gf) | % of Tangled Strokes |
|---|---|---|
| C3 | 208 | 29 |
| C4 | 141 | 13 |
| C5 | 176 | 26 |
| E17 | 155 | 19 |
| E18 | 141 | 17 |
| E19 | 148 | 23 |

Example VI

Anti-Frizz Properties of Cationic Polyglyceryl Compositions and Comparative Examples The personal care compositions of Example IV were tested according to the Anti-Frizz Test, described above. The results, including are given in Table 6.

TABLE 6

Anti-Frizz analysis of Hair Treated with Personal Care Compositions: Comparative Examples (C3-C5) and Inventive Examples (E17-E19)

| Example # | % Frizz at 8 hr | Std Err. (%) |
| --- | --- | --- |
| C3 | 19.94 | 1.13 |
| C4 | 19.11 | 1.29 |
| C5 | 13.65 | 1.04 |
| E17 | 17.99 | 1.29 |
| E18 | 10.93 | 0.80 |
| E19 | 12.24 | 2.56 |

Example VII

Preparation of Comparative and Inventive Personal Care Compositions

Personal care formulations were prepared using inventive and comparative compositions of Example I. In addition, comparative personal care formulations were prepared using Glucquat™ 125, Polyaldo® 10-1-O, Polyaldo® 10-1-L, Natrulon® H-10, as well as no humectant.

The formulations were prepared as follows: to a beaker fitted with a mechanical stirrer and hotplate, water, ammonium lauryl sulfate, and ammonium laureth sulfate were added. This was mixed at low-medium speed and heat was slowly applied to the batch to increase the temperature to 75° C. When the batch reached 75° C., cocamide MEA was added. Heating was stopped after the ingredients were completely dissolved and the batch was allowed to cool to approx. 25° C., while mixing was continued at medium speed. When the batch reached 25° C., sodium chloride and DMDM hydantoin were added and mix until completely dissolved. pH was adjusted to 6.4±0.2 using citric acid or sodium hydroxide solution. After the pH was adjusted a particular commercially-available C-PG/test material was added. Water was added in q.s. to 100%. The composition was mixed at low-medium speed. If the composition was hazy, it was placed in a sealed jar in an oven and heated to 50° C. until clear. The comparative compositions (and active weight percentages of ingredients) are shown in the Table 7a while inventive examples are shown in Table 7b-d.

Natrulon H-10 and Polyaldo® are available from Lonza Group of Allendale, N.J. Standapol® and Comperlan are available from Cognis Corp. (now BASF) of Ambler, Pa.

TABLE 7a

Comparative Personal Care Compositions.

| Test Material/ Tradename | Ingredient Name | C6 | C7 | C8 | C9 | C10 | C11 | C12 |
| --- | --- | --- | --- | --- | --- | --- | --- | --- |
| Control (no C-PG) | Control (no C-PG) | — | — | — | — | — | — | — |
| Polyaldo 10-1-O KFG | PG-10-1-O | — | 2.00 | — | — | — | — | — |
| Polyaldo 10-1-L KFG | PG-10-1-L | — | — | 2.00 | — | — | — | — |
| Natrulon H-10 | PG-10 | — | — | — | 2.00 | — | — | — |
| Glucquat 125 | Lauryl methyl gluceth-10 hydroxypropyldimonium | — | — | — | — | 2.00 | — | — |
| C1 | (TM) PG-10 | — | — | — | — | — | 2.00 | — |
| C2 | (TM)$_3$ PG-10 | — | — | — | — | — | — | 2.00 |
| Standapol A | Ammonium Lauryl Sulfate | 10.92 | 10.92 | 10.92 | 10.92 | 10.92 | 10.92 | 10.92 |
| Standapol EA-2 | Ammonium Laureth Sulfate | 4.39 | 4.39 | 4.39 | 4.39 | 4.39 | 4.39 | 4.39 |
| Comperlan 100 | Cocamide MEA | 1.24 | 1.24 | 1.24 | 1.24 | 1.24 | 1.24 | 1.24 |
| Sodium Chloride | Sodium Chloride | 0.40 | 0.40 | 0.40 | 0.40 | 0.40 | 0.40 | 0.40 |
| Glydant | DMDM Hydantoin | 0.06 | 0.06 | 0.06 | 0.06 | 0.06 | 0.06 | 0.06 |
| Sodium Hydroxide solution (20%) | Sodium Hydroxide | q.s. | q.s. | q.s. | q.s. | q.s. | q.s. | q.s. |
| Citric Acid solution (20%) | Citric Acid | q.s. | q.s. | q.s. | q.s. | q.s. | q.s. | q.s. |
| Puriied Water | Water | q.s. | q.s. | q.s. | q.s. | q.s. | q.s. | q.s. |

TABLE 7b

Inventive Personal Care Compositions.

| Test Material/ Tradename | Ingredient Name | E20 | E21 | E22 | E23 | E24 |
| --- | --- | --- | --- | --- | --- | --- |
| E1 | (CD)$_1$ PG-10 | 2.00 | — | — | — | — |
| E2 | (CD)$_2$ PG-10 | — | 2.00 | — | — | — |
| E4 | (LD)$_1$ PG-10 | — | — | 2.00 | — | — |
| E5 | (LD)$_1$(TM)$_2$ PG-10 | — | — | — | 2.00 | — |
| E6 | (LD)$_1$(TM)$_2$ PG-10 | — | — | — | — | 2.00 |
| Standapol A | Ammonium Lauryl Sulfate | 10.92 | 10.92 | 10.92 | 10.92 | 10.92 |
| Standapol EA-2 | Ammonium Laureth Sulfate | 4.39 | 4.39 | 4.39 | 4.39 | 4.39 |
| Comperlan 100 | Cocamide MEA | 1.24 | 1.24 | 1.24 | 1.24 | 1.24 |
| Sodium Chloride | Sodium Chloride | 0.40 | 0.40 | 0.40 | 0.40 | 0.40 |
| Glydant | DMDM Hydantoin | 0.06 | 0.06 | 0.06 | 0.06 | 0.06 |
| Sodium Hydroxide solution (20%) | Sodium Hydroxide | q.s. | q.s. | q.s. | q.s. | q.s. |
| Citric Acid solution (20%) | Citric Acid | q.s. | q.s. | q.s. | q.s. | q.s. |
| Purified Water | Water | q.s. | q.s. | q.s. | q.s. | q.s. |

TABLE 7c

Inventive Personal Care Compositions.

| Test Material/Tradename | Ingredient Name | E25 | E26 | E27 | E28 | E29 | E30 |
|---|---|---|---|---|---|---|---|
| E7 | $(CD)_1$ PG-10-1-L | 2.00 | — | — | — | — | — |
| E8 | $(LD)_1$ PG-10-1-L | — | 2.00 | — | — | — | — |
| E9 | $(TM)_1$ PG-10-1-L | — | — | 2.00 | — | — | — |
| E10 | $(TM)_3$ PG-10-1-L | — | — | — | 2.00 | — | — |
| E11 | $(TM)_2$ PG-10-1-L | — | — | — | — | 2.00 | — |
| E12 | $(LD)_1$ PG-10-1-LE | — | — | — | — | — | 2.00 |
| Standapol A | Ammonium Lauryl Sulfate | 10.92 | 10.92 | 10.92 | 10.92 | 10.92 | 10.92 |
| Standapol EA-2 | Ammonium Laureth Sulfate | 4.39 | 4.39 | 4.39 | 4.39 | 4.39 | 4.39 |
| Comperlan 100 | Cocamide MEA | 1.24 | 1.24 | 1.24 | 1.24 | 1.24 | 1.24 |
| Sodium Chloride | Sodium Chloride | 0.40 | 0.40 | 0.40 | 0.40 | 0.40 | 0.40 |
| Glydant | DMDM Hydantoin | 0.06 | 0.06 | 0.06 | 0.06 | 0.06 | 0.06 |
| Sodium Hydroxide solution (20%) | Sodium Hydroxide | q.s. | q.s. | q.s. | q.s. | q.s. | q.s. |
| Citric Acid solution (20%) | Citric Acid | q.s. | q.s. | q.s. | q.s. | q.s. | q.s. |
| Purified Water | Water | q.s. | q.s. | q.s. | q.s. | q.s. | q.s. |

TABLE 7d

Inventive Personal Care Compositions.

| Test Material/Tradename | Ingredient Name | E31 | E32 | E33 | E34 |
|---|---|---|---|---|---|
| E13 | $(CD)_1$ PG-10-1-O | 2.0 | — | — | — |
| E14 | $(LD)_1$ PG-10-1-O | — | 2.0 | — | — |
| E15 | $(TM)_1$ PG-10-1-O | — | — | 2.0 | — |
| E16 | $(LD)_1(TM)_2$ PG-10-1-O | — | — | — | 2.0 |
| Standapol A | Ammonium Lauryl Sulfate | 10.92 | 10.92 | 10.92 | 10.92 |
| Standapol EA-2 | Ammonium Laureth Sulfate | 4.39 | 4.39 | 4.39 | 4.39 |
| Comperlan 100 | Cocamide MEA | 1.24 | 1.24 | 1.24 | 1.24 |
| Sodium Chloride | Sodium Chloride | 0.40 | 0.40 | 0.40 | 0.40 |
| Glydant | DMDM Hydantoin | 0.06 | 0.06 | 0.06 | 0.06 |
| Sodium Hydroxide solution (20%) | Sodium Hydroxide | q.s. | q.s. | q.s. | q.s. |
| Citric Acid solution (20%) | Citric Acid | q.s. | q.s. | q.s. | q.s. |
| Purified Water | Water | q.s. | q.s. | q.s. | q.s. |

Example VIII

Zero Shear Viscosity of Compositions and Comparative Examples

The zero shear viscosity of comparative Examples C6-C12 and Examples E20-E34 were tested according to the Zero Shear Viscosity Test, described above, to determine the thickening efficiency. The results of these tests are shown Table 8 and FIG. 4.

TABLE 8

Zero shear viscosity ($\eta_0$) and relative viscosity ($\eta_{relative}$) of comparative and inventive personal care compositions.

| Example | $\eta_0$ (cP) | Sample | $\eta_{relative}$[1] |
|---|---|---|---|
| C6[2] | 980 | Control | 1.0 |
| C7 | 1590 | PG-10-1-O | 1.6 |
| C8 | 530 | PG-10-1-L | 0.5 |
| C9 | 370 | PG-10 | 0.4 |
| C10 | 60 | Glucquat 125 | 0.06 |
| C11 | 720 | C1 | 0.7 |
| C12 | 1330 | C2 | 1.4 |
| E20 | 9290 | E1 | 9.5 |
| E21 | 15500 | E2 | 15.8 |
| E22 | 10660 | E4 | 10.9 |
| E23 | 5900 | E5 | 6.0 |
| E24 | 7000 | E6 | 7.1 |
| E25 | 12010 | E7 | 12.2 |
| E26 | 10200 | E8 | 10.4 |
| E27 | 1420 | E9 | 1.4 |
| E28 | 4470 | E10 | 4.6 |
| E29 | 2780 | E11 | 2.8 |
| E30 | 2410 | E12 | 2.5 |
| E31 | 12670 | E13 | 12.9 |
| E32 | 19780 | E14 | 20.2 |
| E33 | 2860 | E15 | 2.9 |
| E34 | 14800 | E16 | 15.1 |

[1] $\eta_{relative} = \dfrac{\eta_{0\ Example}}{\eta_{0\ Base}}$

[2] Sample C6 is the base formula upon which $\eta_{0\ Base}$ is determined from.

Figure 4:
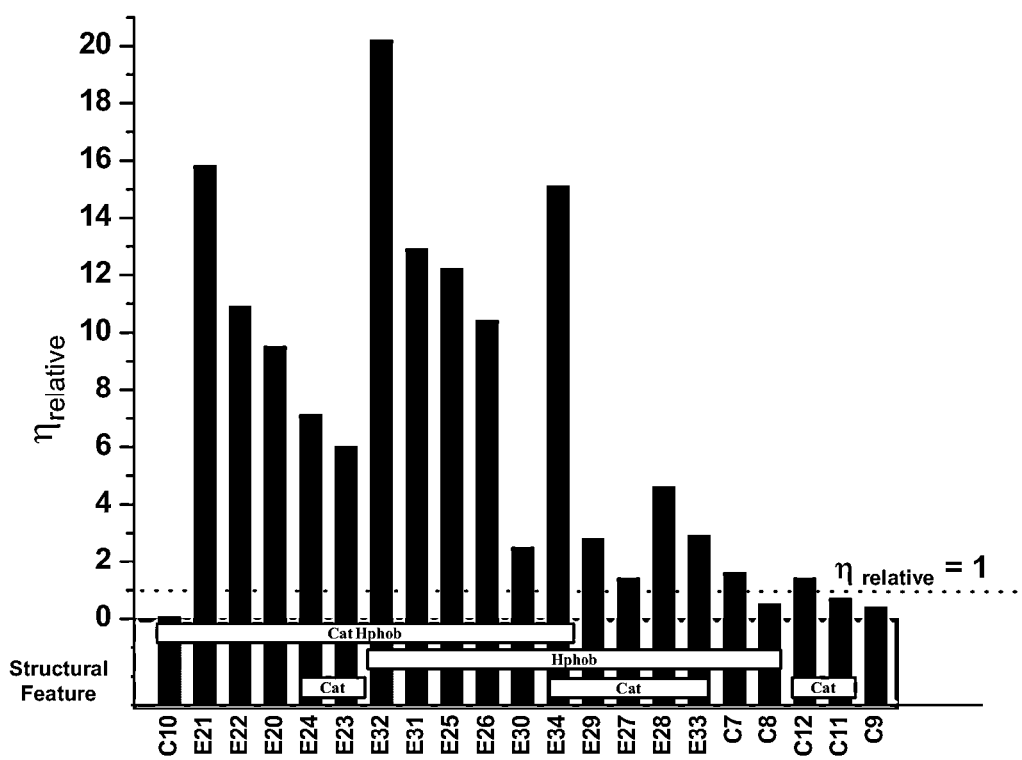
FIG. 4 is a graphical depiction of the relative viscosities of certain compositions of the present invention and comparable compositions.

FIG. 4 depicts the $\eta_{relative}$ of 2 wt % active inventive and comparative materials in a cleansing base formulation (Comparative Example C6). The dashed line indicates an $\eta_{relative}$ of 1. Structural features of the 2 wt % additive material are noted as white horizontal bars transversing samples which contain the feature. Samples may contain 0-3 structural features: Cat-Hphob=($L_2$-$R_2$—N—[($R_3$)($R_4$)(Hphob$_2$)]), Cat=($L_3$-$R_5$—N—[($R_6$)($R_7$)($R_8$)]), and/or Hphob=($L_1$-$R_1$-Hphob$_1$).

As can be seen in FIG. 4, cationic polyglyceryl compositions that include a cationic hydrophobic group (—$R_1$—N—[($R_2$)($R_3$)(Hphob$_2$)]) showed the greatest viscosity increases. This finding is particularly surprising given that Comparative Example, C10 which included Glucquat™ 125, which has a cationic hydrophobic group but contains node structure having ethylene oxide repeat units rather than glyceryl repeat units, results in a material which significantly thins the base formula ($\eta_{relative}$=0.06).

Example IX

Preparation of Comparative and Inventive Personal Care Compositions

Personal care formulations were prepared using select inventive compositions of Example I. In addition, comparative personal care formulations were prepared using Polyaldo® 10-1-O, Polyaldo® 10-1-L, and Natrulon® H-10.

The following personal care compositions, Examples E35-E46, were prepared. The concentrations and particular C-PG are listed in Table 9a while comparative formulations are listed in Tables 9b and 9c.

TABLE 9a

Inventive Personal Care Compositions.

| Test Material/ Tradename | Ingredient Name | E35 | E36 | E37 | E38 | E39 | E40 | E41 | E42 | E43 | E44 | E45 | E46 |
|---|---|---|---|---|---|---|---|---|---|---|---|---|---|
| E1 | $(CD)_1$ PG-10 | 0.50 | 1.0 | 3.5 | 5.0 | — | — | — | — | — | — | — | — |
| E14 | $(LD)_1$ PG-10-1-O | — | — | — | — | 0.50 | 1.0 | 3.5 | 5.0 | — | — | — | — |
| E9 | $(TM)_1$ PG-10-1-L | — | — | — | — | — | — | — | — | 0.50 | 1.0 | 3.5 | 5.0 |
| Standapol A | Ammonium Lauryl Sulfate | 10.92 | 10.92 | 10.92 | 10.92 | 10.92 | 10.92 | 10.92 | 10.92 | 10.92 | 10.92 | 10.92 | 10.92 |
| Standapol EA-2 | Ammonium Laureth Sulfate | 4.39 | 4.39 | 4.39 | 4.39 | 4.39 | 4.39 | 4.39 | 4.39 | 4.39 | 4.39 | 4.39 | 4.39 |
| Comperlan 100 | Cocamide MEA | 1.24 | 1.24 | 1.24 | 1.24 | 1.24 | 1.24 | 1.24 | 1.24 | 1.24 | 1.24 | 1.24 | 1.24 |
| Sodium Chloride | Sodium Chloride | 0.40 | 0.40 | 0.40 | 0.40 | 0.40 | 0.40 | 0.40 | 0.40 | 0.40 | 0.40 | 0.40 | 0.40 |
| Glydant | DMDM Hydantoin | 0.06 | 0.06 | 0.06 | 0.06 | 0.06 | 0.06 | 0.06 | 0.06 | 0.06 | 0.06 | 0.06 | 0.06 |
| Sodium Hydroxide solution (20%) | Sodium Hydroxide | q.s. | q.s. | q.s. | q.s. | q.s. | q.s. | q.s. | q.s. | q.s. | q.s. | q.s. | q.s. |
| Citric Acid solution (20%) | Citric Acid | q.s. | q.s. | q.s. | q.s. | q.s. | q.s. | q.s. | q.s. | q.s. | q.s. | q.s. | q.s. |
| Purified Water | Water | q.s. | q.s. | q.s. | q.s. | q.s. | q.s. | q.s. | q.s. | q.s. | q.s. | q.s. | q.s. |

TABLE 9b

Comparative Personal Care Compositions.

| Test Material/ Tradename | Ingredient Name | C13 | C14 | C15 | C16 | C17 | C18 | C19 | C20 | C21 | C22 | C23 | C24 |
|---|---|---|---|---|---|---|---|---|---|---|---|---|---|
| Natrulon H-10 | PG-10 | 0.50 | 1.0 | 3.5 | 5.0 | — | — | — | — | — | — | — | — |
| Polyaldo 10-1-L | PG-10-1-L | — | — | — | — | 0.50 | 1.0 | 3.5 | 5.0 | — | — | — | — |
| Polyaldo 10-1-O | PG-10-1-O | — | — | — | — | — | — | — | — | 0.50 | 1.0 | 3.5 | 5.0 |
| Standapol A | Ammonium Lauryl Sulfate | 10.92 | 10.92 | 10.92 | 10.92 | 10.92 | 10.92 | 10.92 | 10.92 | 10.92 | 10.92 | 10.92 | 10.92 |
| Standapol EA-2 | Ammonium Laureth Sulfate | 4.39 | 4.39 | 4.39 | 4.39 | 4.39 | 4.39 | 4.39 | 4.39 | 4.39 | 4.39 | 4.39 | 4.39 |
| Comperlan 100 | Cocamide MEA | 1.24 | 1.24 | 1.24 | 1.24 | 1.24 | 1.24 | 1.24 | 1.24 | 1.24 | 1.24 | 1.24 | 1.24 |
| Sodium Chloride | Sodium Chloride | 0.40 | 0.40 | 0.40 | 0.40 | 0.40 | 0.40 | 0.40 | 0.40 | 0.40 | 0.40 | 0.40 | 0.40 |
| Glydant | DMDM Hydantoin | 0.06 | 0.06 | 0.06 | 0.06 | 0.06 | 0.06 | 0.06 | 0.06 | 0.06 | 0.06 | 0.06 | 0.06 |
| Sodium Hydroxide solution (20%) | Sodium Hydroxide | q.s. | q.s. | q.s. | q.s. | q.s. | q.s. | q.s. | q.s. | q.s. | q.s. | q.s. | q.s. |
| Citric Acid solution (20%) | Citric Acid | q.s. | q.s. | q.s. | q.s. | q.s. | q.s. | q.s. | q.s. | q.s. | q.s. | q.s. | q.s. |
| Purified Water | Water | q.s. | q.s. | q.s. | q.s. | q.s. | q.s. | q.s. | q.s. | q.s. | q.s. | q.s. | q.s. |

TABLE 9c

Comparative Personal Care Compositions.

| Test Material/ Tradename | Ingredient Name | C25 | C26 | C27 | C28 |
|---|---|---|---|---|---|
| Glucquat 125 | Lauryl methyl gluceth-10 hydroxypropyldimonium | 0.50 | 1.0 | 3.5 | 5.0 |
| Standapol A | Ammonium Lauryl Sulfate | 10.92 | 10.92 | 10.92 | 10.92 |
| Standapol EA-2 | Ammonium Laureth Sulfate | 4.39 | 4.39 | 4.39 | 4.39 |

TABLE 9c-continued

Comparative Personal Care Compositions.

| Test Material/ Tradename | Ingredient Name | C25 | C26 | C27 | C28 |
|---|---|---|---|---|---|
| Comperlan 100 | Cocamide MEA | 1.24 | 1.24 | 1.24 | 1.24 |
| Sodium Chloride | Sodium Chloride | 0.40 | 0.40 | 0.40 | 0.40 |
| Glydant | DMDM Hydantoin | 0.06 | 0.06 | 0.06 | 0.06 |
| Sodium Hydroxide solution (20%) | Sodium Hydroxide | q.s. | q.s. | q.s. | q.s. |
| Citric Acid solution (20%) | Citric Acid | q.s. | q.s. | q.s. | q.s. |
| Purified Water | Water | q.s. | q.s. | q.s. | q.s. |

The results are shown in FIG. 1 and Table 10. With the exception of E42, formulas containing inventive examples resulted in a thickened formula ($\eta_{relative}$>1). As seen in FIG. 1, formulations including E14 [(LD)$_1$ PG-10-1-O (closed triangles)] and E1 [(CD)$_1$ PG-10 (closed squares)] have a maximum effect on viscosity between 2.0-3.5 wt %. Both of these examples contain cationic-hydrophobes. Conversely, inventive examples containing a hydrophobic group (Hphob$_1$) and a cationic group (—R$_4$—N—[(R$_5$)(R$_6$)(R$_7$)])[(TM)$_1$ PG-10-1-L, E9 (formulas represented by closed circles)] exhibit a slight increase in viscosity from doses of 0.5-2.0 wt % and a more significant increase as the dose is raised to 5.0 wt %.

The comparative examples containing Glucquat™ 125 (open diamonds), PG-10 (open squares), and PG-10-1-L (open circles) resulted in a thinned material ($\eta_{relative}$<1) with the exception of C17 (0.5 wt % PG-10-1-L). Thus, the only comparative other than C17 capable of thickening was PG-10-1-O (open triangles)

TABLE 10

Zero shear viscosity ($\eta_0$) and relative viscosity ($\eta_{relative}$) of inventive personal care compositions and comparative personal care compositions

| Example | Ingredient Name | $\eta_0$ (cP) | Wt % Active | $\eta_{relative}$[1] |
|---|---|---|---|---|
| E35 | (CD)$_1$ PG-10 | 2480 | 0.5 | 2.5 |
| E36 | (CD)$_1$ PG-10 | 3090 | 1.0 | 3.2 |
| E37 | (CD)$_1$ PG-10 | 18500 | 3.5 | 18.9 |
| E38 | (CD)$_1$ PG-10 | 4360 | 5.0 | 4.4 |
| E39 | (LD)$_1$ PG-10-1-O | 2770 | 0.5 | 2.8 |
| E40 | (LD)$_1$ PG-10-1-O | 4420 | 1.0 | 4.5 |
| E41 | (LD)$_1$ PG-10-1-O | 3380 | 3.5 | 3.4 |
| E42 | (LD)$_1$ PG-10-1-O | 620 | 5.0 | 0.6 |
| E43 | (TM)$_1$ PG-10-1-L | 1400 | 0.5 | 1.4 |
| E44 | (TM)$_1$ PG-10-1-L | 1320 | 1.0 | 1.3 |
| E45 | (TM)$_1$ PG-10-1-L | 2830 | 3.5 | 2.9 |
| E46 | (TM)$_1$ PG-10-1-L | 4600 | 5.0 | 4.7 |
| C13 | PG-10 | 750 | 0.5 | 0.8 |
| C14 | PG-10 | 450 | 1 | 0.5 |
| C15 | PG-10 | 90 | 3.5 | <0.1 |
| C16 | PG-10 | 60 | 5 | <0.1 |
| C17 | PG-10-1-L | 1190 | 0.5 | 1.2 |

TABLE 10-continued

Zero shear viscosity ($\eta_0$) and relative viscosity ($\eta_{relative}$) of inventive personal care compositions and comparative personal care compositions

| Example | Ingredient Name | $\eta_0$ (cP) | Wt % Active | $\eta_{relative}$[1] |
|---|---|---|---|---|
| C18 | PG-10-1-L | 670 | 1 | 0.7 |
| C19 | PG-10-1-L | 650 | 3.5 | 0.7 |
| C20 | PG-10-1-L | 740 | 5 | 0.8 |
| C21 | PG-10-1-O | 1360 | 0.5 | 1.4 |
| C22 | PG-10-1-O | 1370 | 1 | 1.4 |
| C23 | PG-10-1-O | 2710 | 3.5 | 2.8 |
| C24 | PG-10-1-O | 5040 | 5 | 5.1 |
| C25 | Glucquat 125 | 260 | 0.5 | 0.3 |
| C26 | Glucquat 125 | 130 | 1 | 0.1 |
| C27 | Glucquat 125 | 38 | 3.5 | <0.1 |
| C28 | Glucquat 125 | 35 | 5 | <0.1 |

What is claimed is:

1. A polyglyceryl composition comprising:
N-(2-hydroxypropyl)-N,N-dimethyllauryl-1-ammonium chloride decaglyceryl ether, and wherein the polyglyceryl composition has an average degree of polymerization determined by hydroxyl value testing (DP$_{OH}$) of from about 3 to about 20 and comprises less than 2% of an electrolyte.

2. The polyglyceryl composition of claim 1 having a DP$_{OH}$ of from about 3 to about 10.

3. The polyglyceryl composition of claim 1 having a DP$_{OH}$ of from about 5 to about 10.

4. The polyglyceryl composition of claim 1 having a DP$_{OH}$ of about 10.

5. A personal care composition comprising:
a solvent,
a polyglyceryl composition, comprising N-(2-hydroxypropyl)-N,N-dimethyllauryl-1-ammonium chloride decaglyceryl ether, and
at least one material selected from the group consisting of surfactants, chelating agents, emollients, humectants, conditioners, preservatives, opacifiers, fragrances, and combinations of two or more thereof,
wherein the personal care composition comprises less than 5 percent by weight of an electrolyte, and wherein the polyglyceryl composition has an average degree of polymerization determined by hydroxyl value testing (DPOH) of from about 3 to about 20.

6. The personal care composition of claim 5 having a DP$_{OH}$ of about 10.

7. The personal care composition of claim 5 wherein the electrolyte is selected from the group consisting of sodium chloride, ammonium chloride and magnesium chloride.

8. The personal care composition of claim 5 comprising less than 2% by weight of the electrolyte.

9. The personal care composition of claim 5 having a pH from 5 to 9.

10. The polyglyceryl composition of claim 1 wherein the electrolyte is selected from the group consisting of sodium chloride, ammonium chloride and magnesium chloride.

11. The polyglyceryl composition of claim 1 having a pH from 5 to 9.

* * * * *